(12) United States Patent
Searle et al.

(10) Patent No.: US 9,125,975 B2
(45) Date of Patent: Sep. 8, 2015

(54) USER-ACTUATED STORAGE ASSEMBLY FOR INJECTION DEVICE

(75) Inventors: Gary Searle, Norfolk, MA (US);
Charles Hwang, Wellesley, MA (US)

(73) Assignee: Becton, Dickinson and Company, Franlkin Lakes, NJ (US)

( * ) Notice: Subject to any disclaimer, the term of this patent is extended or adjusted under 35 U.S.C. 154(b) by 1066 days.

(21) Appl. No.: 13/205,452

(22) Filed: Aug. 8, 2011

(65) Prior Publication Data
US 2012/0041417 A1 Feb. 16, 2012

Related U.S. Application Data

(60) Provisional application No. 61/344,542, filed on Aug. 16, 2010.

(51) Int. Cl.
*A61M 5/32* (2006.01)
*A61M 5/00* (2006.01)

(52) U.S. Cl.
CPC .......... *A61M 5/002* (2013.01); *A61M 2005/004* (2013.01)

(58) Field of Classification Search
CPC ................. A61M 2005/004; A61M 5/002
USPC .................. 206/363–366; 604/232–234, 263, 604/192–199
See application file for complete search history.

(56) References Cited

U.S. PATENT DOCUMENTS

| | | | |
|---|---|---|---|
| 5,304,193 A | 4/1994 | Zhadanov | |
| 5,522,797 A | 6/1996 | Grimm | |
| 5,586,553 A | 12/1996 | Halili | |
| 5,682,233 A | 10/1997 | Brinda | |
| 5,829,589 A | 11/1998 | Nguyen | |
| 5,871,494 A | 2/1999 | Simons | |
| 5,971,966 A | 10/1999 | Lav | |
| 6,117,109 A | 9/2000 | Eggers | |
| 6,306,152 B1 | 10/2001 | Verdonk | |
| 6,332,871 B1 | 12/2001 | Douglas | |
| 6,346,094 B2 | 2/2002 | West | |
| 6,591,124 B2 | 7/2003 | Sherman | |
| 6,612,111 B1 | 9/2003 | Hodges | |
| 6,616,616 B2 | 9/2003 | Fritz | |
| 7,041,068 B2 | 5/2006 | Freeman | |
| 7,134,550 B2 | 11/2006 | Groth | |

(Continued)

FOREIGN PATENT DOCUMENTS

| | | |
|---|---|---|
| DE | 10 2008 046205 | 2/2009 |
| EP | 1 757 320 | 2/2007 |
| WO | 2009016161 | 2/2009 |

OTHER PUBLICATIONS

European Search Report issued Dec. 12, 2012 for Application No. 11177495.6-2320.

*Primary Examiner* — Rebecca E Eisenberg
(74) *Attorney, Agent, or Firm* — Roylance, Abrams Berdo & Goodman, L.L.P.

(57) ABSTRACT

A storage assembly is removably connectable to a drug delivery device. A first chamber is disposed in the housing. A plurality of penetrating members are stored in the first chamber. A second chamber is disposed in the housing for storing the plurality of penetrating members after being used in an injection. A transfer drum disposed in the housing transfers one of the penetrating members from the first chamber to an injection position and from the injection position to the second chamber following an injection.

22 Claims, 25 Drawing Sheets

(56) References Cited

U.S. PATENT DOCUMENTS

| | | |
|---|---|---|
| 7,244,266 B2 | 7/2007 | Garthe |
| 2003/0015444 A1 | 1/2003 | Molin |
| 2003/0144608 A1 | 7/2003 | Kojima |
| 2003/0153939 A1 | 8/2003 | Fritz |
| 2005/0199647 A1 | 9/2005 | Muto |
| 2006/0161194 A1 | 7/2006 | Freeman |
| 2006/0195128 A1* | 8/2006 | Alden et al. .................. 606/181 |
| 2007/0093864 A1 | 4/2007 | Pugh |
| 2007/0112367 A1 | 5/2007 | Olson |
| 2007/0167875 A1* | 7/2007 | Freeman et al. .............. 600/583 |
| 2007/0260271 A1 | 11/2007 | Freeman |
| 2008/0039795 A1 | 2/2008 | Slate |
| 2008/0058732 A1 | 3/2008 | Harris |

\* cited by examiner

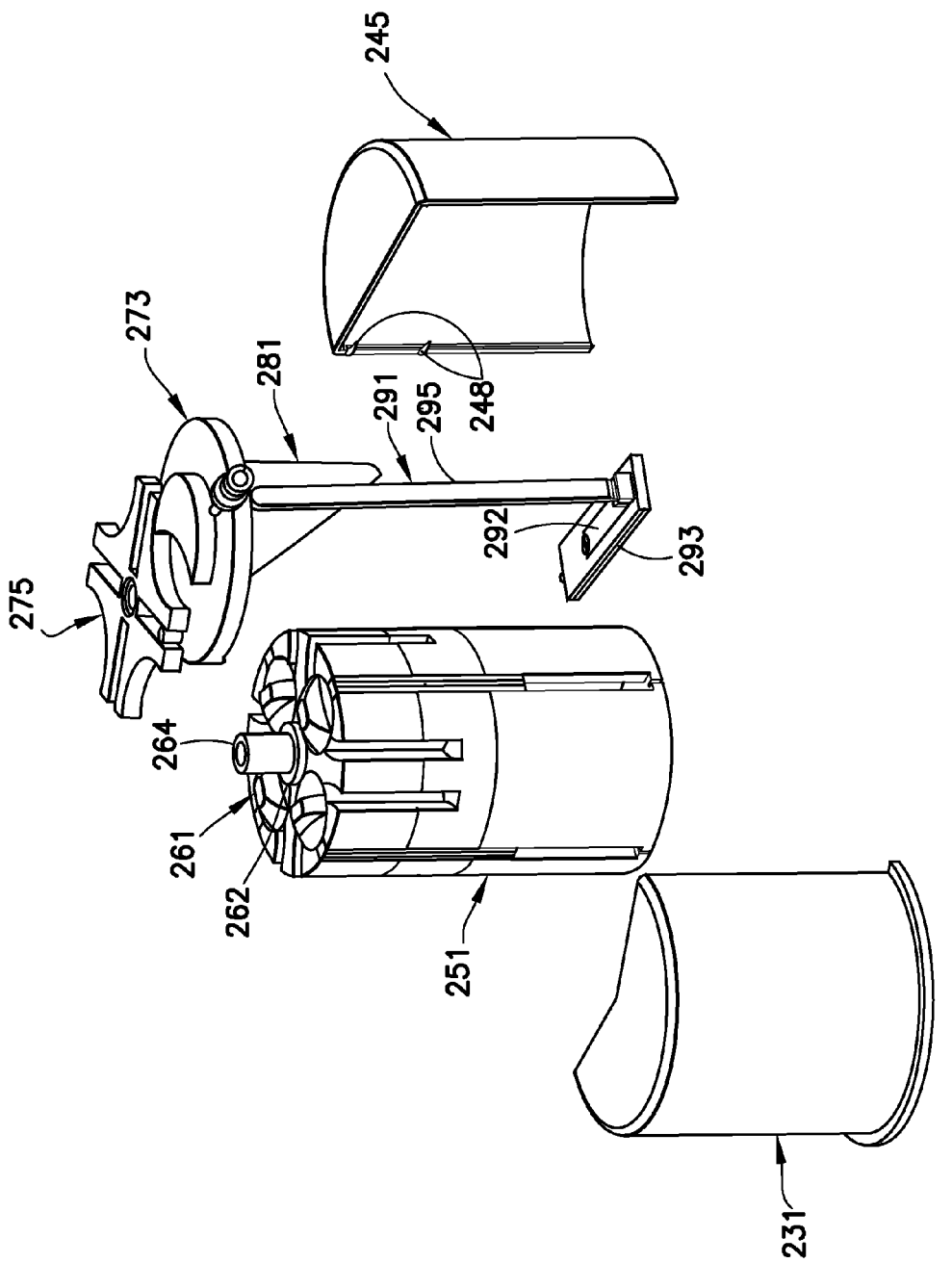

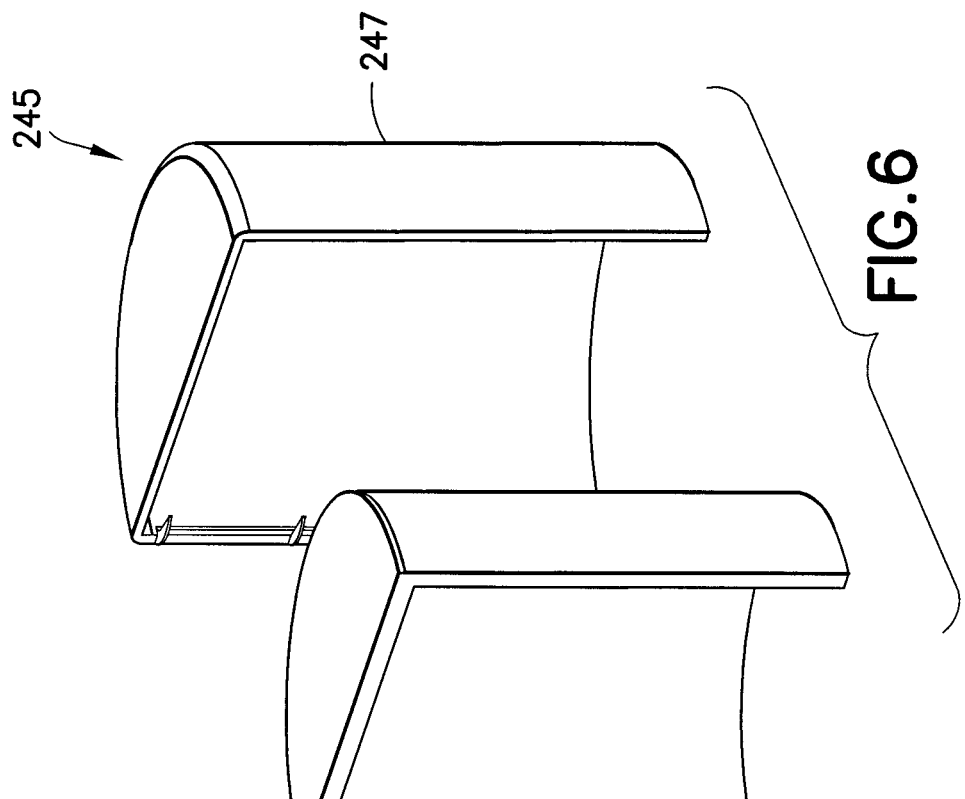
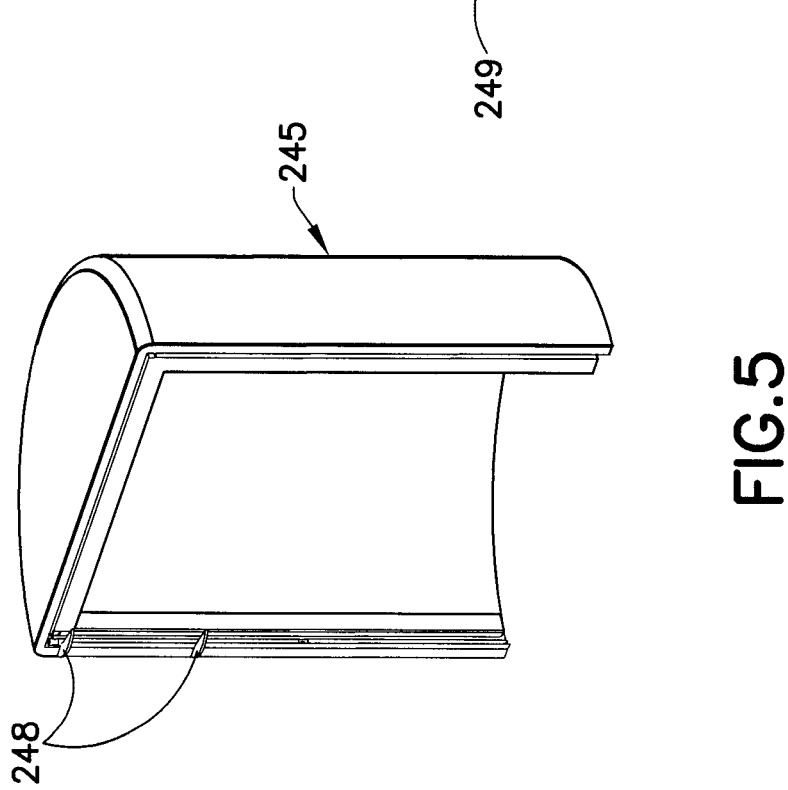

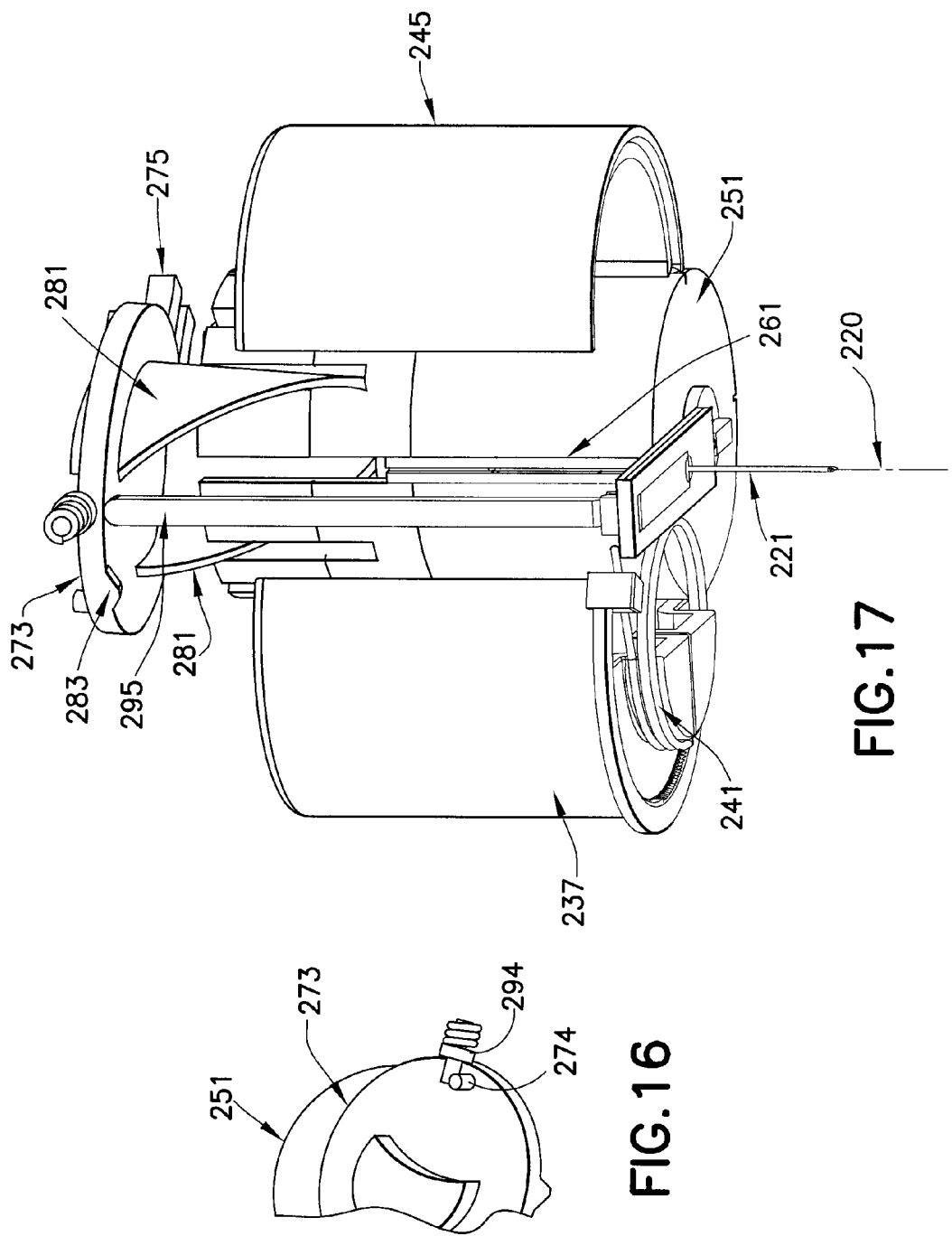

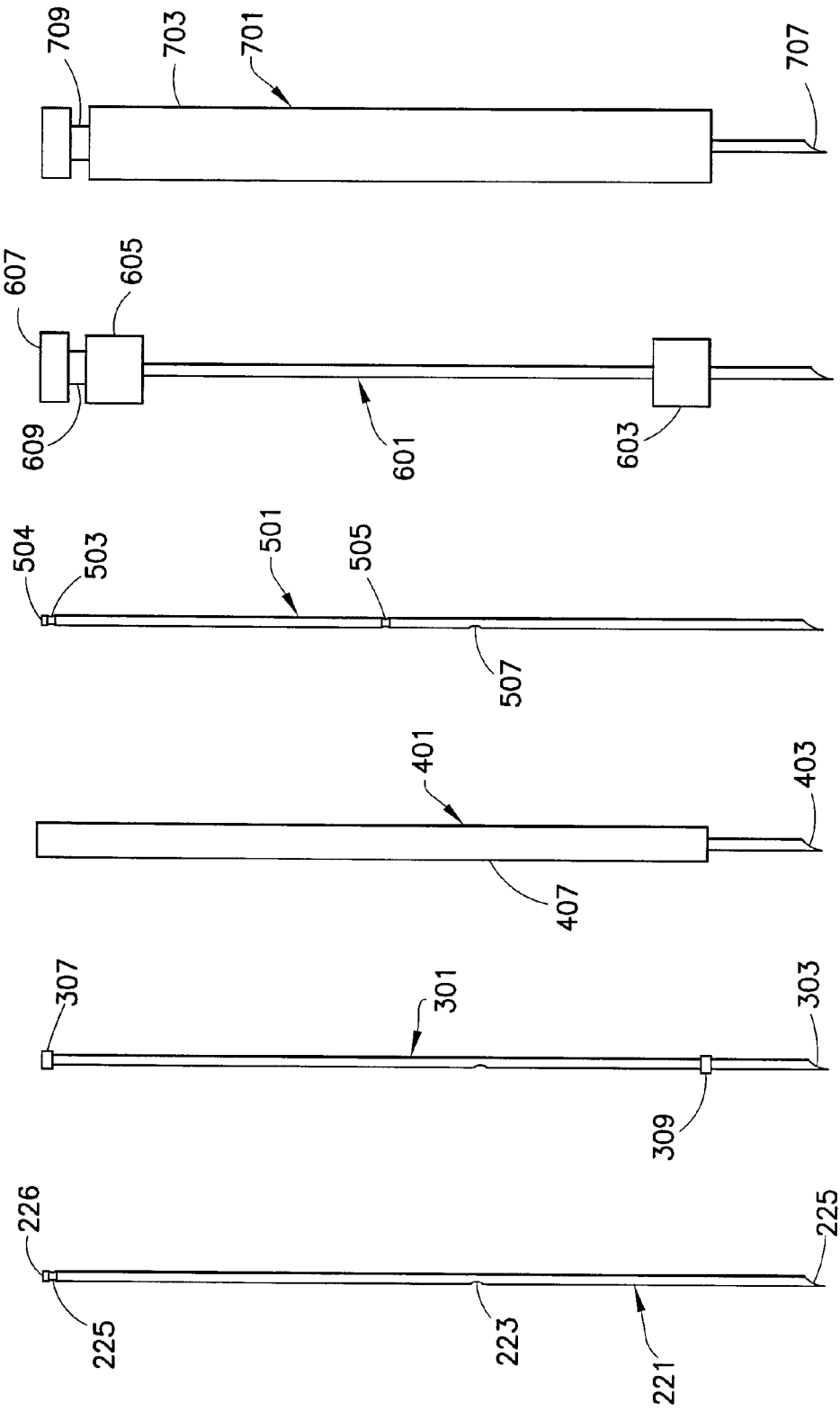

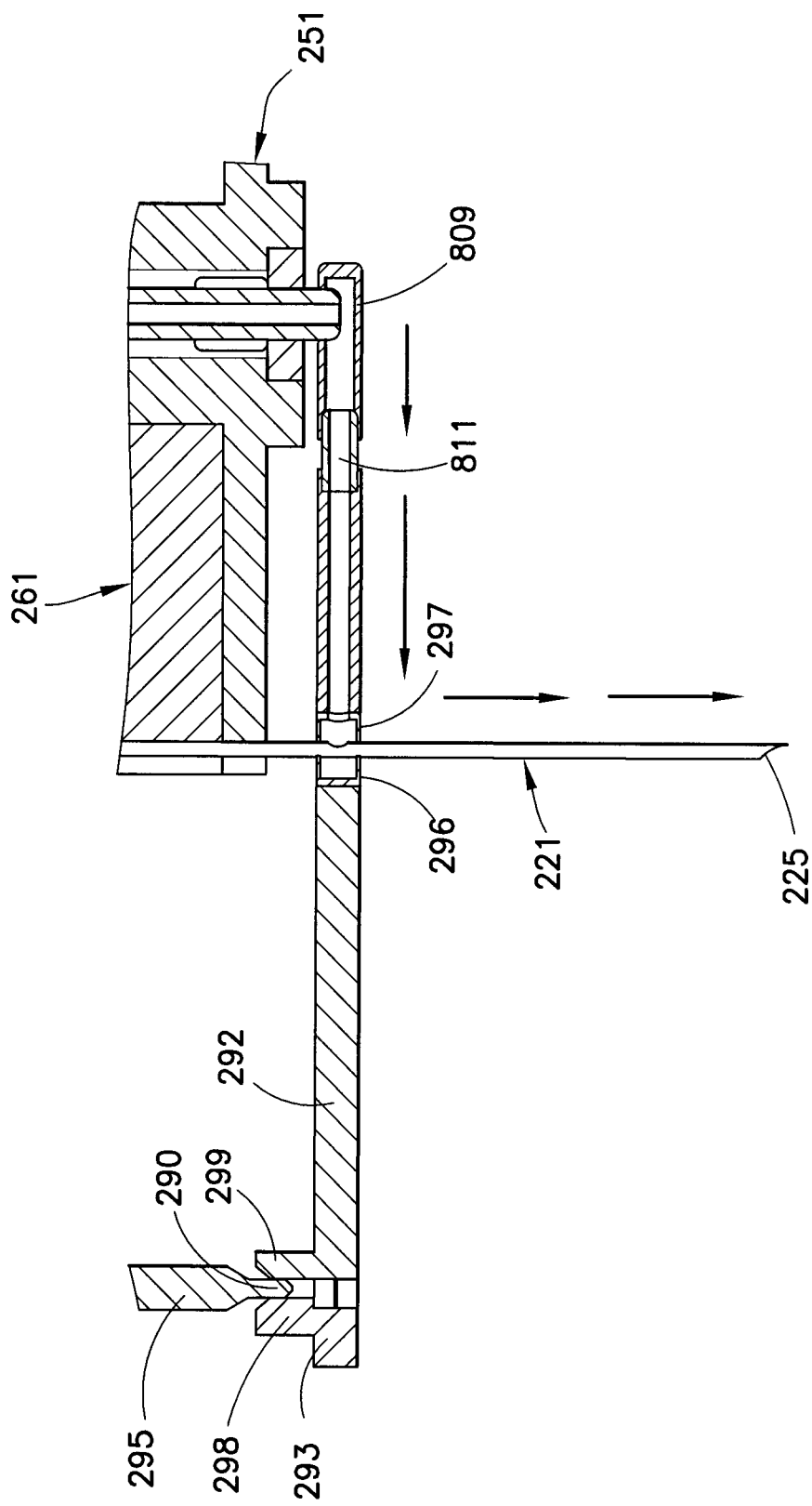

USER-ACTUATED STORAGE ASSEMBLY FOR INJECTION DEVICE

CROSS REFERENCE TO RELATED APPLICATION

This application claims the benefit under 35 U.S.C. §119(e) of U.S. Provisional Application Ser. No. 61/344,542, filed Aug. 16, 2010, which is hereby incorporated by reference in its entirety.

FIELD OF THE INVENTION

The present invention relates to a user-actuated storage assembly for an injection device. More particularly, the present invention relates to a storage assembly for storing a plurality of cannulas and dispensing a cannula when actuated by a user. Still more particularly, the present invention relates to such a storage assembly for storing used cannulas.

BACKGROUND OF THE INVENTION

In certain circumstances, it is desirable to inject medication directly into human tissue. Typically, syringes or pen injection devices are used to inject medicaments into tissue areas, such as the intramuscular tissue layer, the subcutaneous tissue layer, and the intradermal tissue layer.

The assembly and operation of a typical pen injection device is described in commonly-assigned U.S. Pat. No. 7,645,264, which is hereby incorporated by reference in its entirety.

Pen injection devices, such as an exemplary pen injector 100, as shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is employed by the user to securely hold the pen injector 100 in a shirt pocket, purse, or other suitable location.

FIG. 1B is an exploded view of an exemplary drug delivery pen shown in FIG. 1A. The dose knob/button 24 has a dual purpose and is used to both set the dosage of the medication to be injected and to inject the dosed medicament via the lead screw 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail herein as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used such as attaching to the cartridge. To protect a user, or anyone who handles the pen injection device 100, an outer cover 69, which attaches to the hub 20, covers the hub. An inner shield 59 covers the patient needle 11 within the outer cover 69. The inner shield 59 can be secured to the hub 20 to cover the patient needle 11 by any suitable means, such as an interference fit or a snap fit. The outer cover 69 and inner shield 59 are removed prior to use. The cap 21 fits snugly against outer sleeve 13 to allow a user to securely carry the drug delivery pen 100.

A pen needle, which includes the hub 20, needle 11, outer shield 69 and inner shield 59, is typically used for a single injection and is then disposed of. Accordingly, patients must carry several pen needles to perform multiple injections over a period of time. Pen needles are generally stored loose in a container so that there is no simple and convenient way for a patient to keep multiple pen needles together. Accordingly, a need exists for a user to easily and conveniently carry a plurality of cannulas for use with a drug delivery pen.

Pen needles are usually sold individually packaged inside a plastic cover (such as outer shield 69) with a label (not shown) covering the opening in the cover to provide a sterility barrier. To use the pen needle assembly 10, the user removes a sterile cover (not shown) on the outer shield 69, twists the hub 20 onto the lower housing 17, removes the outer shield 69, and then finally removes the inner shield 59. Accordingly, the user must remove needle hub packaging, including the inner and outer shields 59 and 69, to connect a pen needle to a drug delivery pen to ready the device for an injection. This process must be repeated for each successive injection, in addition to properly disposing of the pen needle used for the previous injection.

Accordingly, a need exists for a storage assembly that stores a plurality of cannulas before and after their use. A need also exists for such a storage assembly that dispenses a cannula when actuated by a user and connects the dispensed cannula to the drug delivery pen.

Existing multi-needle injection devices are typically of two configurations. The first configuration retains the cannulas in a flexible bandolier, e.g, a bullet bandolier. The bandolier or cannula is then incrementally fed to the injection axis. The second configuration retains the cannulas in a magazine or cartridge. Either the magazine is incrementally moved to align a cannula with the injection axis, or a cannula is removed and transferred to the injection axis. Both configurations reduce the size of the design envelope of the pen needle from the traditional single-use design envelope. However, both configurations still incorporate a needle hub, which increases the volumetric envelope of the cannula used for either the bandolier or magazine configurations. The volumetric envelope is further increased by the bandolier or magazine, thereby significantly limiting the number of single-use cannulas that can be retained relative to the overall size of the device. Accordingly, a need exists for a storage assembly for an injection device that increases the number of cannulas that can be stored therein.

SUMMARY OF THE INVENTION

In accordance with an aspect of the present invention, a storage assembly stores new cannulas for use by a drug delivery pen.

In accordance with another aspect of the present invention, the storage assembly also stores used cannulas.

In accordance with another aspect of the present invention, the storage assembly is conducive to being carried by a user.

In accordance with yet another aspect of the present invention, the storage assembly dispenses a new cannula when actuated by a user and connects the dispensed cannula to the drug delivery pen.

A storage assembly according to exemplary embodiments of the present invention stores new and used cannulas, and dispenses a new cannula when actuated by a patient. The storage assembly can be integrally formed with the drug delivery pen. Alternatively, the storage assembly can be removably connected to the drug delivery pen. The storage assembly, or revolver, dispenses a single cannula from a magazine each time the storage assembly is mechanically actuated by a user.

The foregoing objectives are attained by a storage assembly for use with a drug delivery device. A first chamber is disposed in the housing. A plurality of penetrating members are stored in the first chamber. A second chamber is disposed in the housing for storing the plurality of penetrating members after being used in an injection. A transfer drum disposed in the housing transfers one of the penetrating members from the first chamber to an injection position and from the injection position to the second chamber following the injection.

The foregoing objectives are also attained by a method of performing an injection with a drug delivery device. One of a plurality of penetrating members is transferred from a first chamber to a transfer drum by rotating the drug delivery device. The transferred penetrating member is moved to an injection position by continued rotation of the drug delivery device. A medicament is injected from the drug delivery device through the transferred penetrating member into an injection site. The used penetrating member is transferred to a second chamber.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which:

FIG. 4 is an exploded perspective view of the storage assembly components of FIG. 3;

FIG. 5 is a perspective view of the out-feed subassembly of FIG. 4;

FIG. 6 is an exploded perspective view of the out-feed subassembly of FIG. 5;

FIG. 16 is an enlarged perspective view of the spring loaded pin;

FIG. 17 is a perspective view from below of the assembled storage assembly of FIGS. 2A-2C without the outer cover;

FIGS. 26A-26F are side elevational views of various cannula configurations;

FIG. 30 is an enlarged elevational view in cross section of the hub jaws in the closed position.

Throughout the drawings, like reference numbers will be understood to refer to like parts, components and structures.

DETAILED DESCRIPTION OF THE EXEMPLARY EMBODIMENTS

Figure 2C:
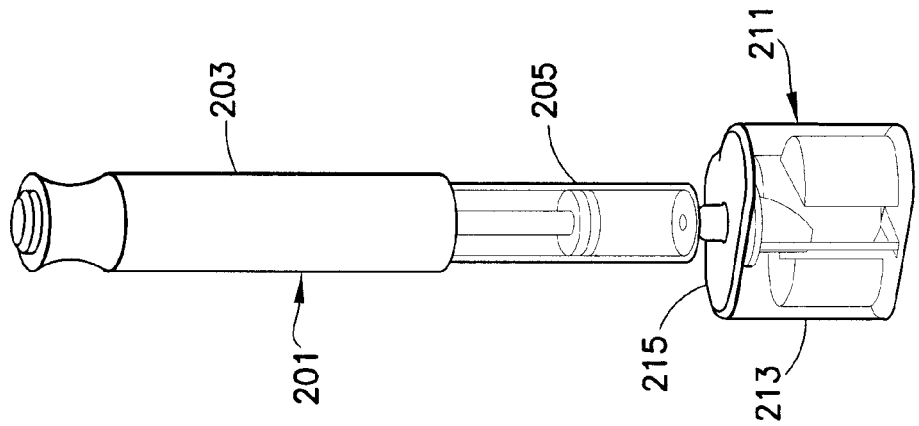
FIGS. 2A, 2B and 2C are front elevational, side elevational and perspective views of a revolver in accordance with exemplary embodiment of the present invention connected to an existing drug delivery pen.
Figure 2B:
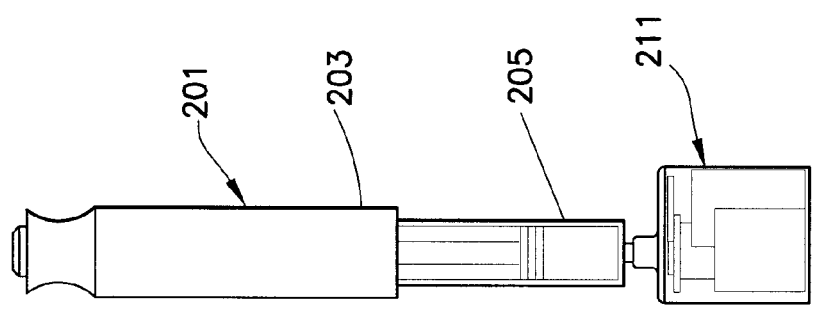
Figure 2A:
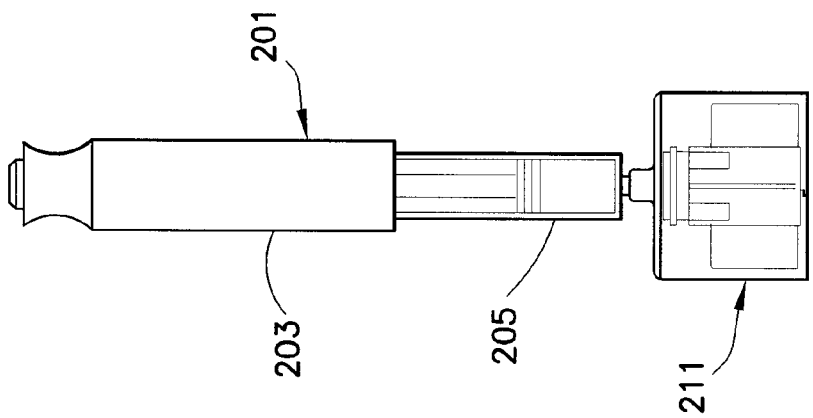

FIGS. 2A-2C illustrate a storage assembly 211 in accordance with an exemplary embodiment of the present invention for use with a drug delivery pen 201. The cannula 221 used with the storage assembly 211 of FIGS. 2A-2C as described below is shown in FIG. 26A. Other cannula configurations are shown in FIGS. 26B-26F. To maximize the number of cannulas that can be retained by the storage assembly, the cannulas are preferably not over-molded and the features thereof for feeding and handling are internal to the cylindrical envelope of the cannula. Thus, the cost of the storage assembly is reduced relative to existing multi-needle devices. The manufacturing operations associated with production of the cannulas is simplified and reduced. For example, cannulas in accordance with exemplary embodiments of the present invention do not require hub molding and epoxy assembly.

The storage assembly 211 in accordance with exemplary embodiments of the present invention, as shown, for example, in FIGS. 2A-2C, can retain a large number of cannulas. For example, a storage assembly retaining 100 cannulas allows a user to exchange cannulas three times a day each day for a month, such that the storage assembly only need be refilled monthly. The increase in storage capacity of the storage assembly is obtained in part by using cannulas that are not over-molded or epoxied into plastic molded hubs, thereby increasing the storage capacity of the storage assembly and increasing the number of use cycles of the injection device relative to injection devices using cannulas having integral hubs. Cannula configurations including overmolded hubs are shown in FIGS. 26B, 26E and 26F and increase the cylindrical cannula envelope from a 0.010 inch (0.025 cm) diameter to a 0.060 inch (0.152 cm) diameter, such that the number of cannulas that can be retained in the storage assembly is reduced to between approximately 20 and 30 cannulas. Thus, the injection device including such a storage assembly is a weekly device. However, such an injection device allows more liberal tolerances for the components of the storage assembly.

The over-molded and epoxied hubs used in existing pen needles 20 (FIG. 1B) are replaced with a reusable hub in exemplary embodiments of the present invention. The opening in the reusable hub is variable and controlled with a linear hub cam, such that the opening is larger than the diameter of the cannula while the cannula is being advanced from a transfer drum to the forward-most position. Once the cannula is in the forward-most position, the hub compresses around the cannula to provide a sealed fluid path through the cross-port in the cannula.

Figure 3:
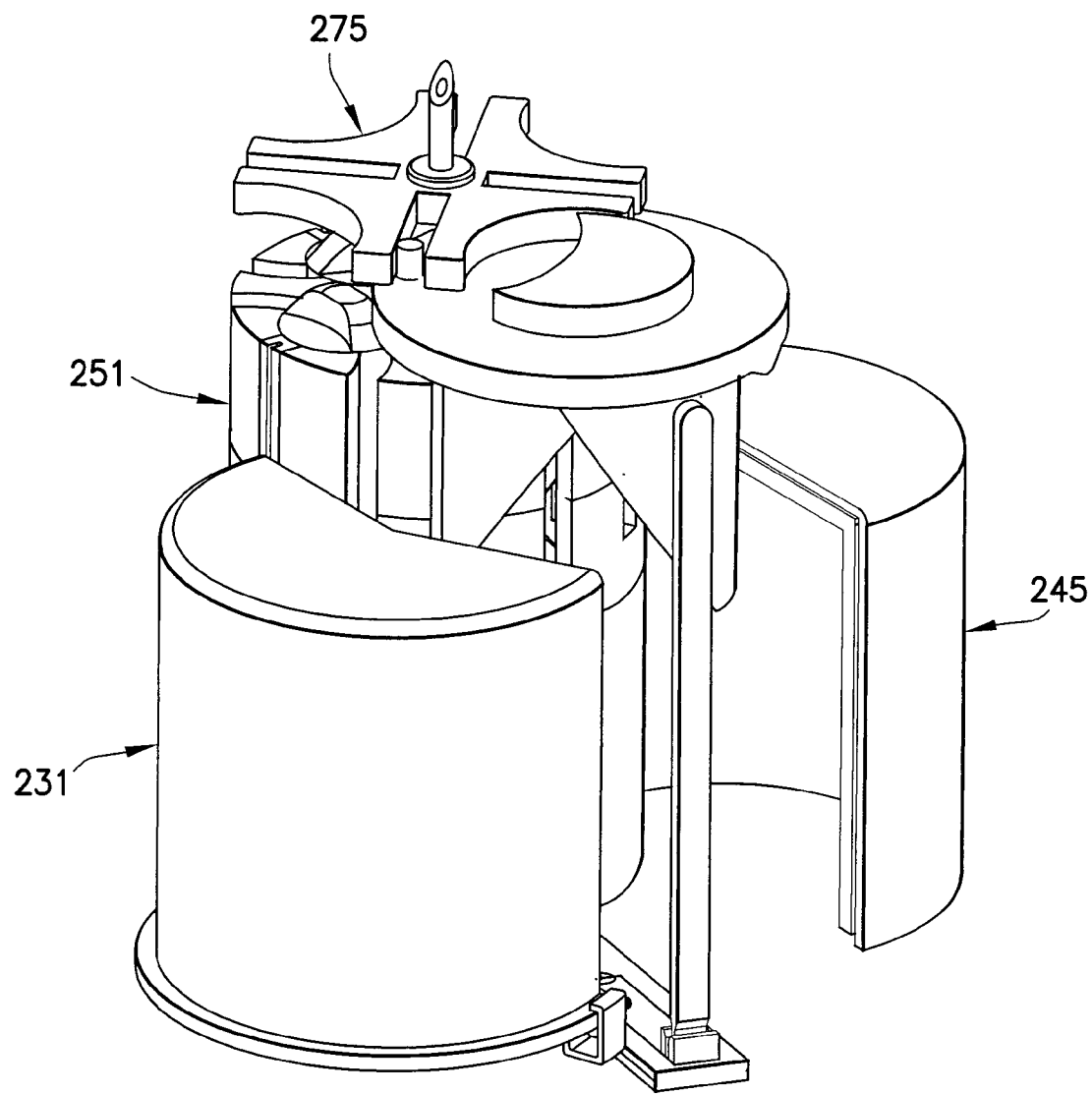
FIG. 3 is a perspective view of the internal components of the storage assembly of FIGS. 2A-2C.
Figure 13:
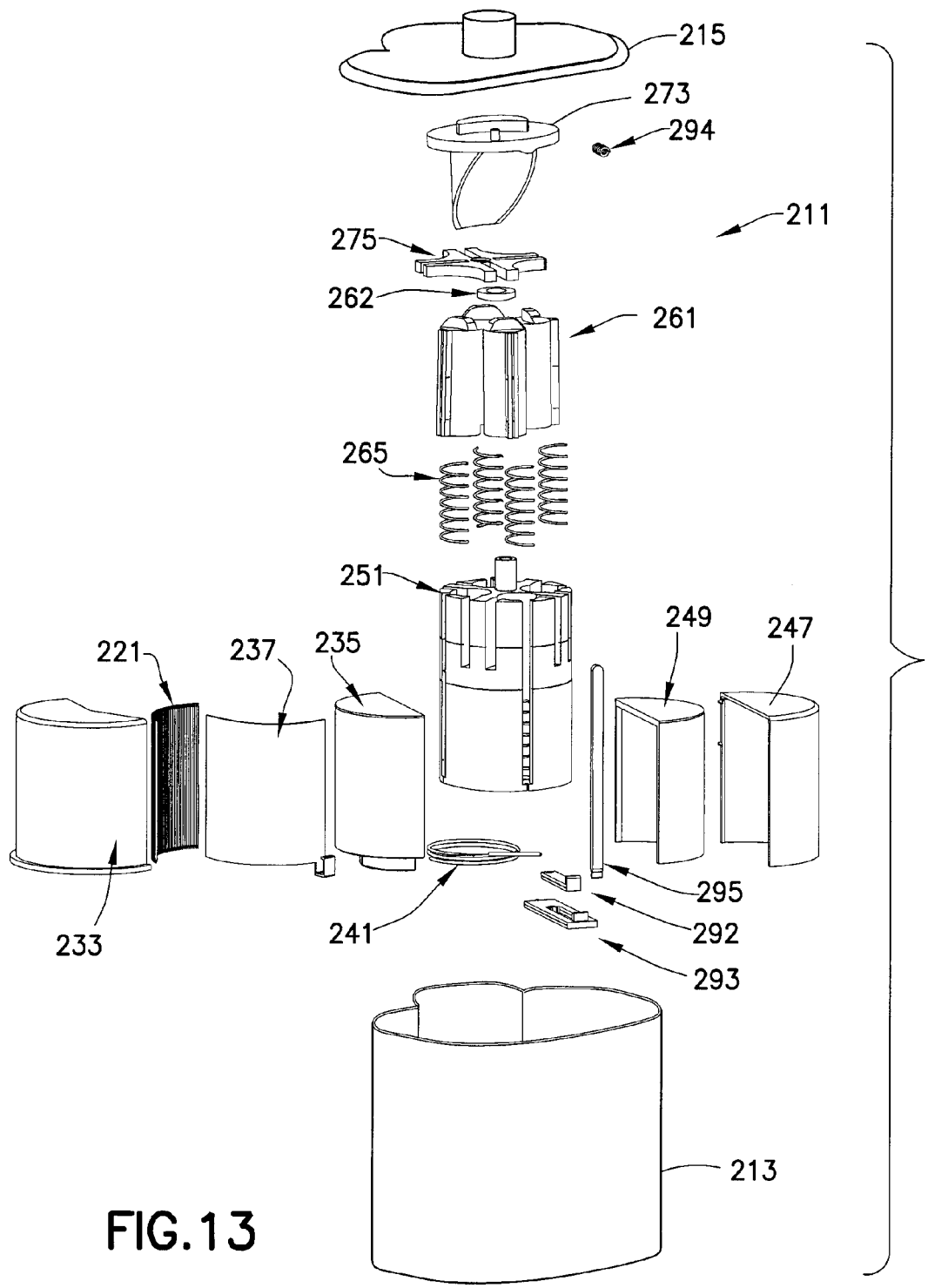
FIG. 13 is an exploded perspective view of the storage assembly of FIGS. 2A-2C.

The storage assembly 211, or revolver, of FIGS. 2A-2C includes an in-feed assembly 231, an in-feed spring (or torsion spring) 241, a transfer drum 251, a plurality of transfer slides 261, a gear assembly 271, a rotary cam 281, a reusable cannula hub 291 and a linear cam 295, as shown in FIGS. 3, 4 and 13. The internal components are disposed in an outer cover 213 having a top 215, which is bonded to the outer cover 213 to seal the storage assembly 211, as shown in FIG. 13. The storage assembly 211 is connectable to the drug delivery pen 201. The storage assembly remains connected to the drug delivery pen 201 during an injection. The used cannulas are stored in an out-feed assembly 245 of the storage assembly 211 while the storage assembly 211 remains connected to the drug delivery pen 201. Accordingly, the storage assembly 211 is removed from the drug delivery pen 201 and the entire storage assembly 211 is properly disposed of when all the cannulas 221 have been used. A new storage assembly 211 containing new cannulas 221 can then be connected to the drug delivery pen 201.

Figure 7:
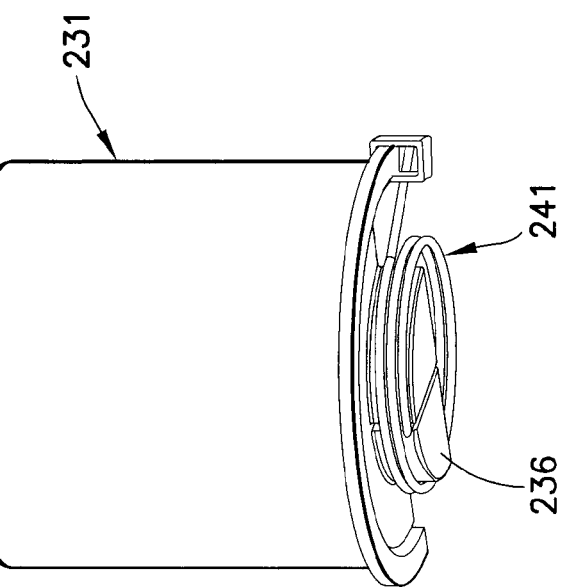
FIG. 7 is a perspective view of the in-feed subassembly of FIG. 4.
Figure 8:
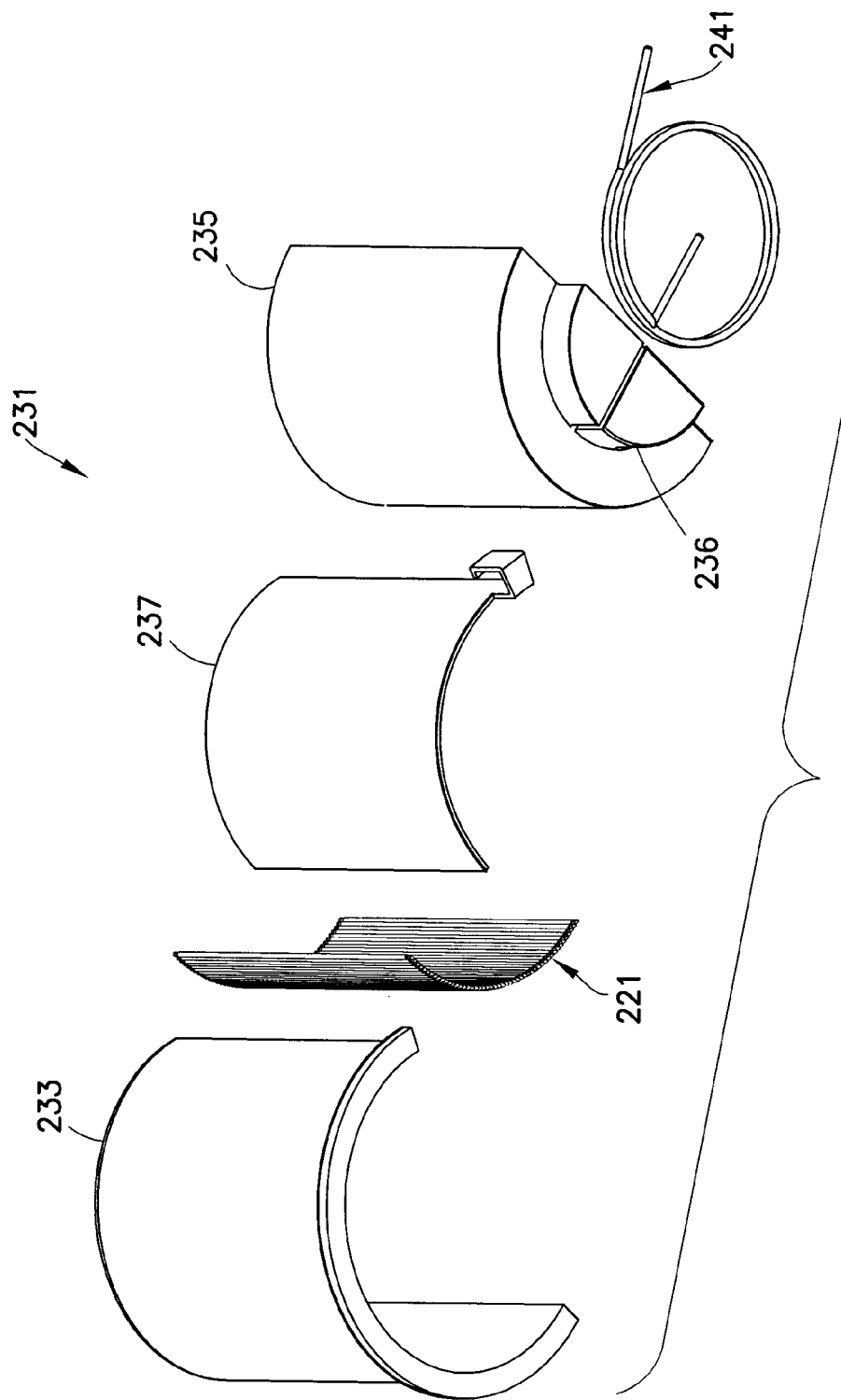
FIG. 8 is an exploded perspective view of the in-feed subassembly of FIG. 7.

The in-feed assembly 231, or magazine, retains the cannulas 221 in a line around the inner perimeter of the in-feed cover 233 adjacent to one another, as shown in FIGS. 7 and 8. The cannulas 221 are disposed between an in-feed cover 233 and an in-feed guide 235. An in-feed blade 237 is disposed between the in-feed cover 233 and the in-feed guide 235 adjacent the last cannula 221.

The in-feed spring 241, or torsion spring, as shown in FIGS. 7 and 8, is connected between a projection 236 of the in-feed guide 235 and the in-feed blade 237. The spring 241 applies constant back pressure to the cannulas 221 in the in-feed assembly 231. The arc-shaped in-feed assembly 231 meets the transfer drum 251 substantially perpendicularly, as shown in FIG. 3. The in-feed spring 241, located approximately at the center of the arc, at the base of the in-feed assembly 231 applies a force to the in-feed blade 237, which contacts the trailing-most cannula 221, thereby applying back pressure to the line of cannulas.

Figure 9:
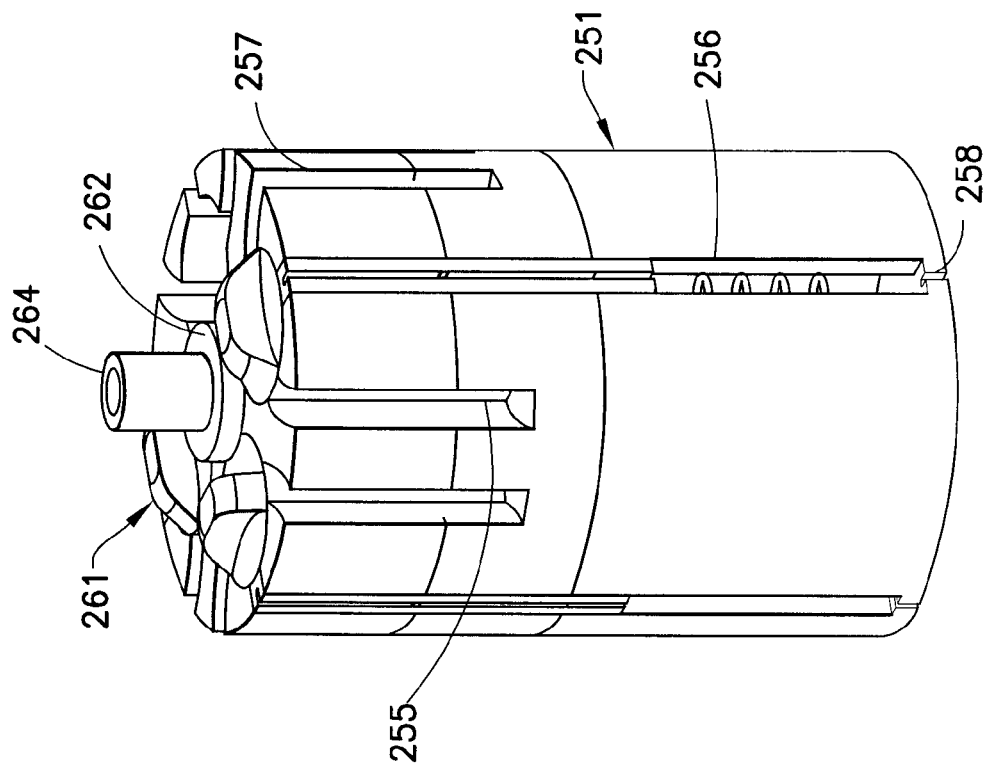
FIG. 9 is a perspective view of the transfer subassembly of FIG. 4.
Figure 10:
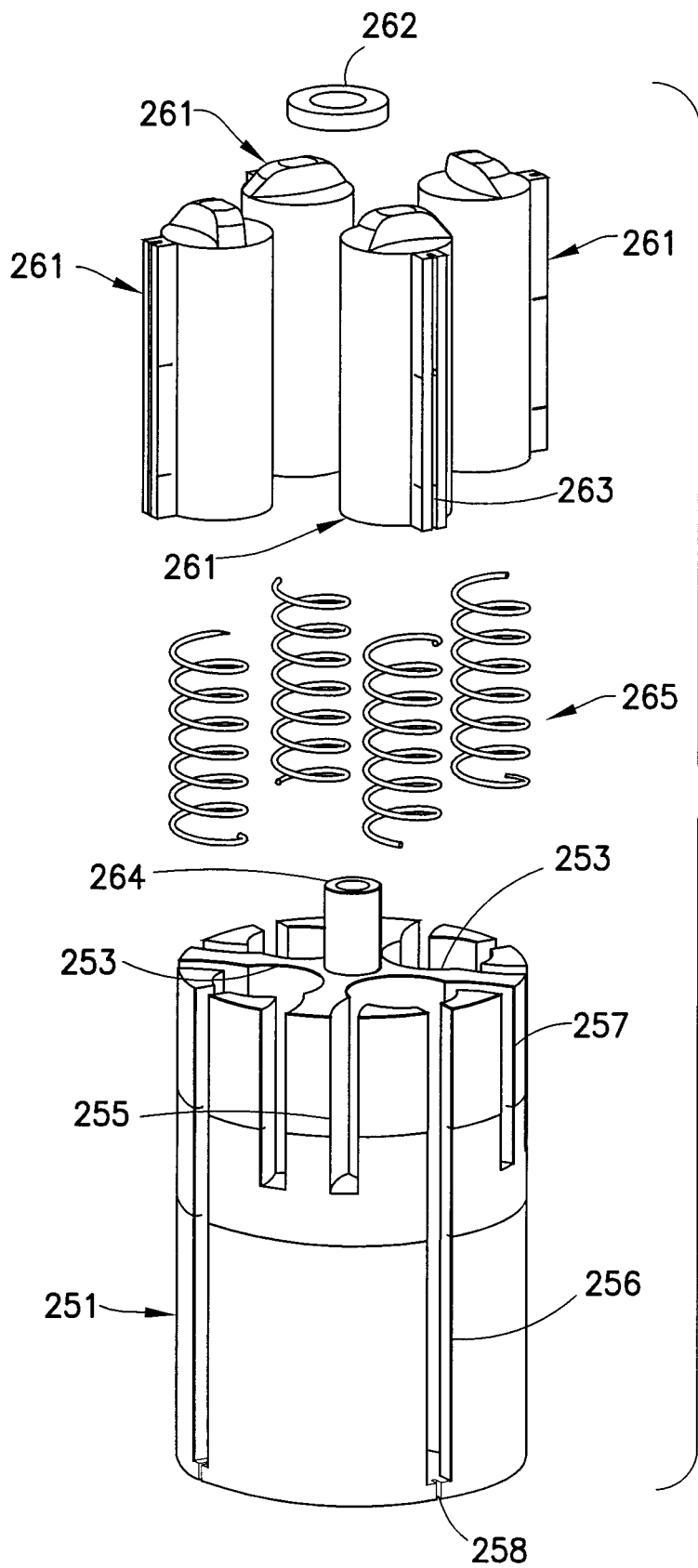
FIG. 10 is an exploded perspective view of the transfer subassembly of FIG. 9.

The transfer drum 251, as shown in FIGS. 9 and 10, indexes the lead-most cannula 221 to and from the injection axis. The transfer drum 251 is restricted from turning in both directions by a pawl or ratchet (not shown), and therefore can only advance a cannula from the in-feed assembly 231 to the injection axis 220, and from the injection axis to the out-feed assembly 245.

The plurality of transfer slides 261 are integral to the transfer drum 251 and retain the indexed cannula 221. Each transfer slide 261 is preferably disposed in one of the openings 253 in the transfer drum 251, as shown in FIG. 10. The transfer slides 261 also advance and retract the retained cannulas 261. As shown in FIGS. 9 and 10, four transfer slides 261 are shown connected to the transfer drum 251. Each transfer slide 261 has a slot 263 for receiving a cannula 221. A return spring 265 is disposed in each transfer drum opening 263 and biases the transfer slide 261 upwardly, as shown in FIG. 9.

Figure 19:
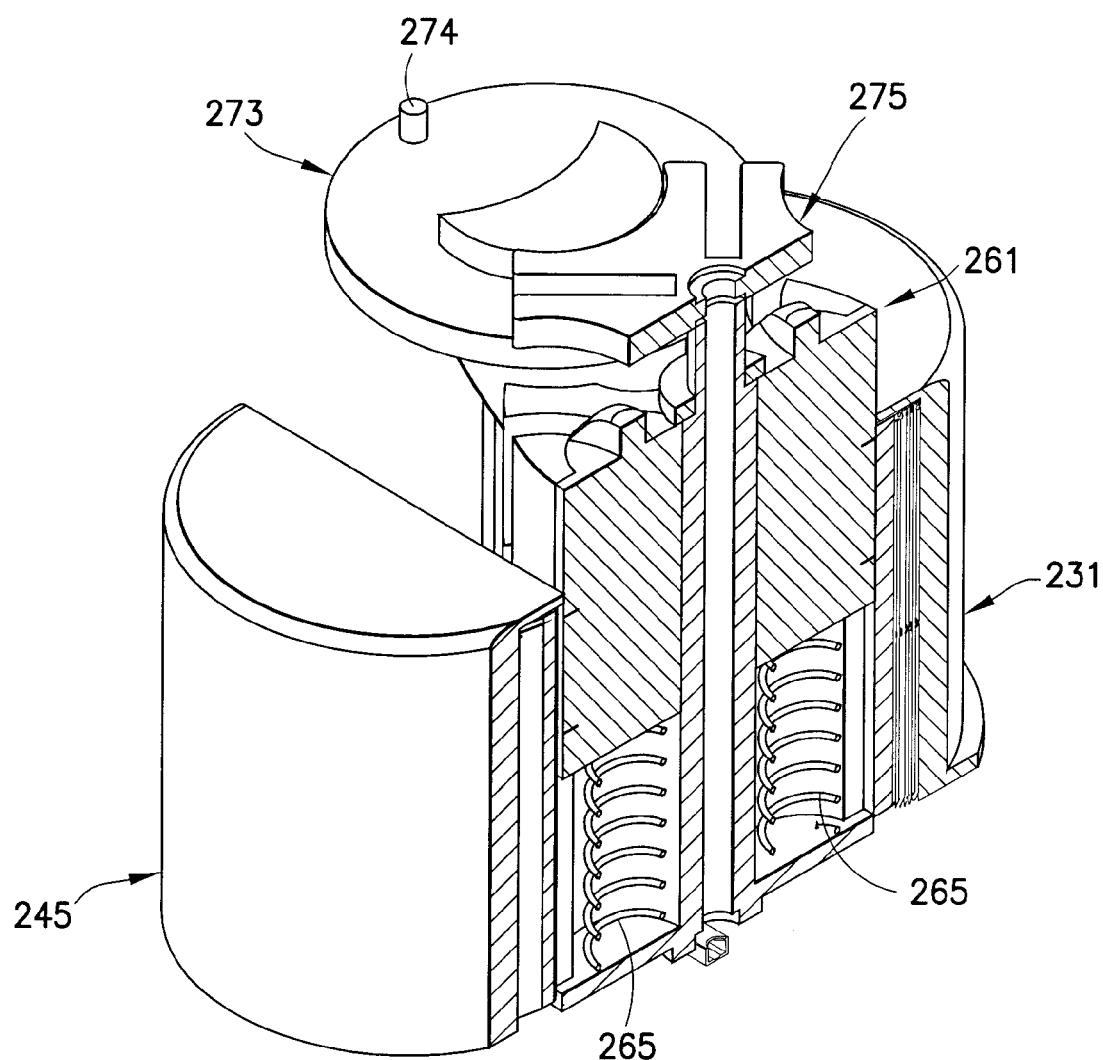
FIG. 19 is a cross-sectional view of the transfer drum of the storage assembly of FIG. 18.

Three slots 255, 256 and 257 are associated with each transfer drum opening 253, as shown in FIGS. 9 and 10. A middle slot 256 is disposed between outer slots 255 and 257. Preferably, the middle slot 256 is longer than the outer slots 255 and 257, which are approximately the same length. The middle slot preferably extends along the entire length of the transfer drum 251, as shown in FIG. 9. The middle slot 256 allows the portion of the transfer slide 261 receiving the cannula 221 to slide therethrough, i.e., the transfer slide slot 263. The outer slots 255 and 257 allow the rotary cam 281 to pass therethrough to contact the transfer slide 261 and move it downwardly, as shown in FIG. 17. When the rotary cam 281 exits the outer slots 255 and 257, the return spring 265 moves the transfer slide upwardly to its original position, as shown in FIG. 19.

A transfer slide retaining ring 262 is disposed over the transfer drum shaft 264, as shown in FIG. 9. The retaining ring 262 limits upward movement of the transfer slides 261 by the return springs 265. The retaining ring 262 extends over a portion of each transfer drum opening 253, thereby limiting upward movement of the transfer slide 261 in the opening 253.

Figure 11:
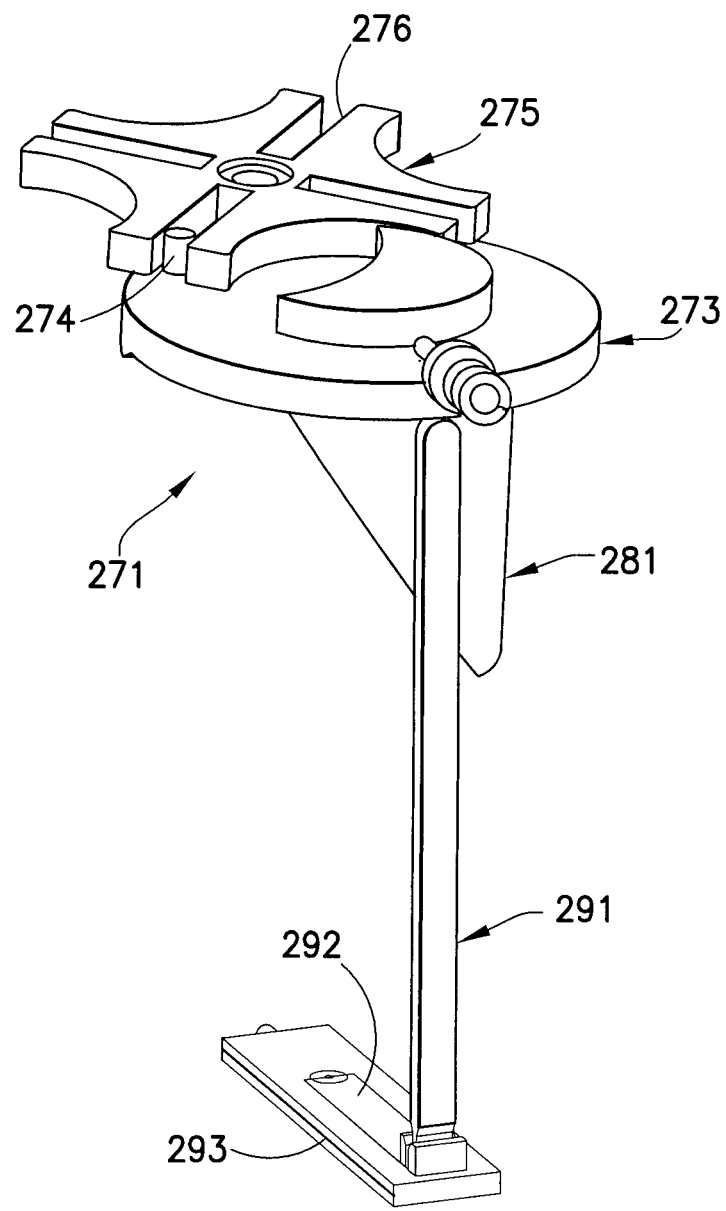
FIG. 11 is a perspective view of the drive subassembly of FIG. 4.
Figure 12:
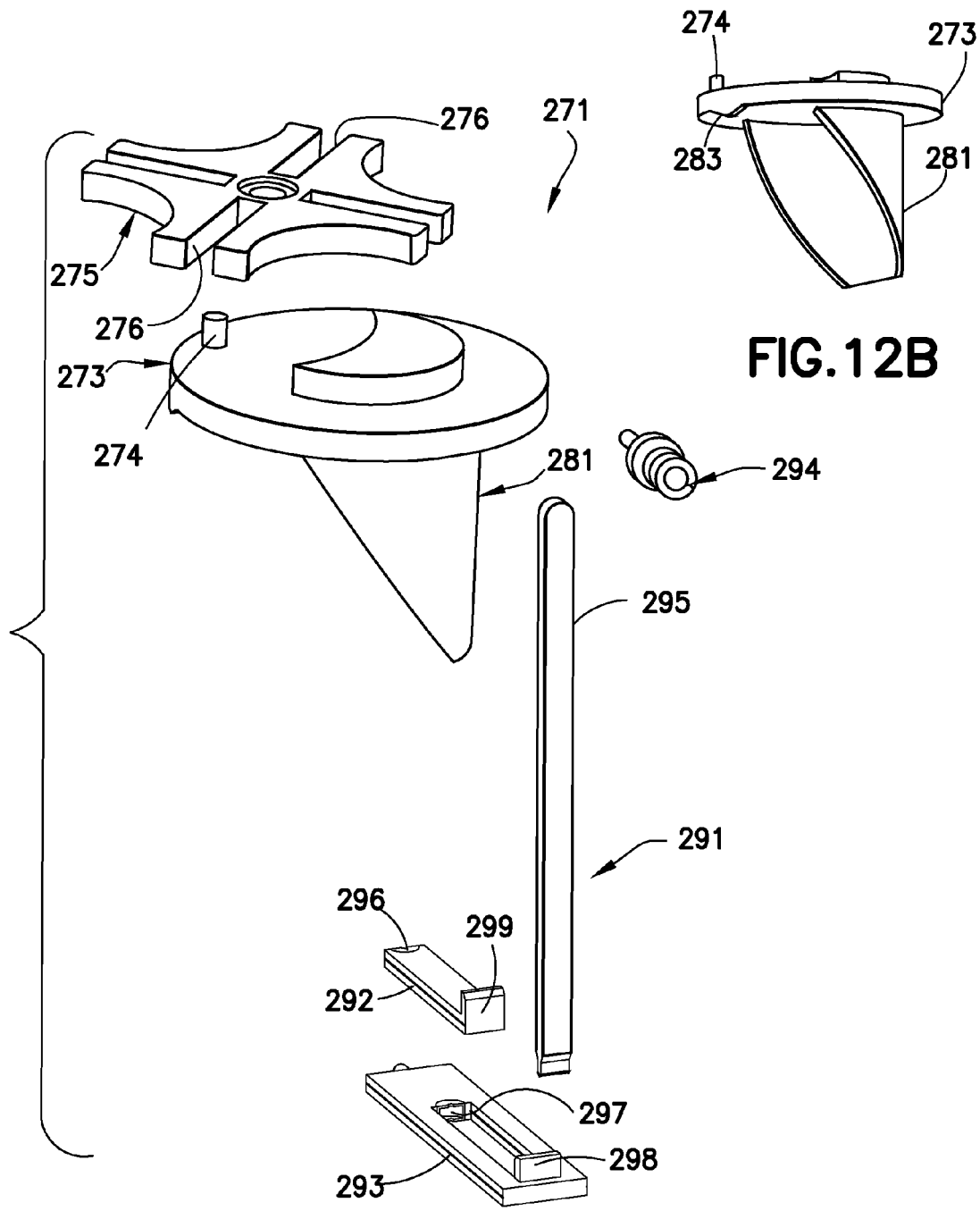
FIG. 12A is an exploded perspective view of the drive subassembly of FIG. 11.
FIG. 12B is a perspective view of the drive gear of FIG. 12.
Figure 14A:
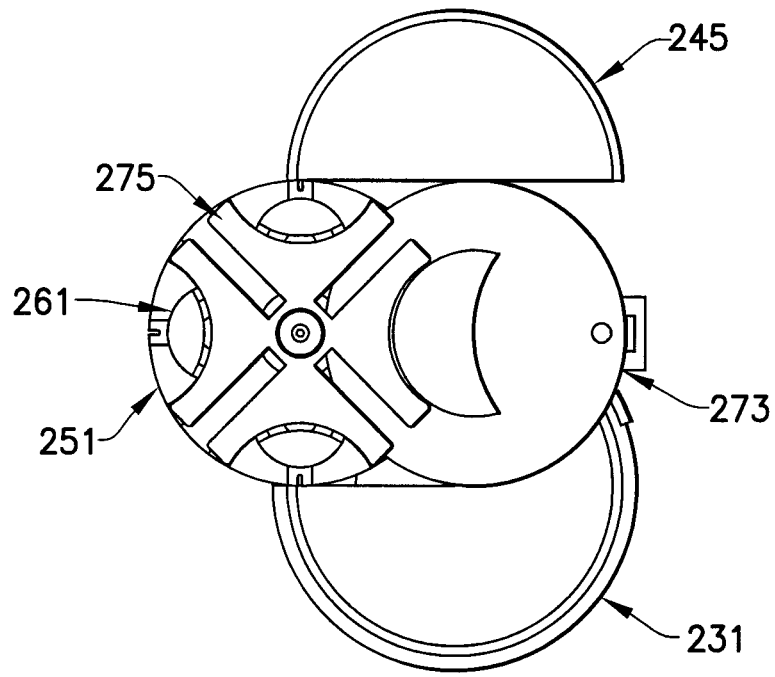
FIGS. 14A and 14B are top plan views of the storage assembly of FIGS. 2A-2C.
Figure 14B:
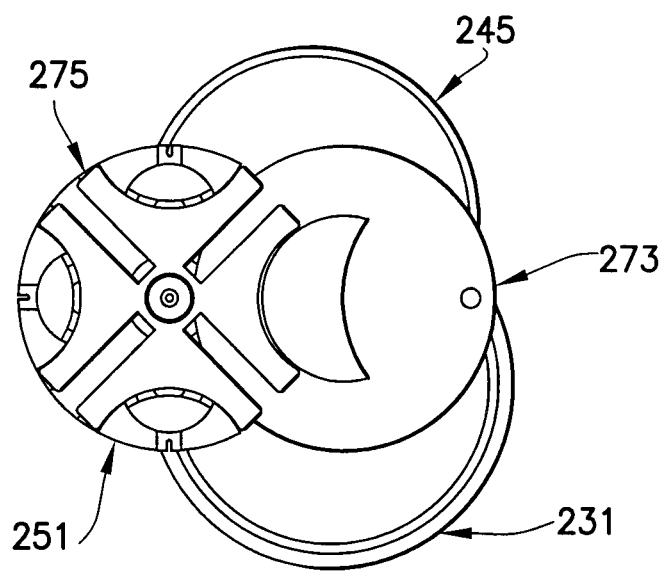

The gear assembly 271, as shown in FIGS. 11, 12 and 12A, controls the index and dwell cycles of the transfer drum 251. The drive gear 273 of the gear assembly 271 is connected to the barrel 203 of the drug delivery pen 201, as shown in FIG. 2C. The driven gear 275 of the gear assembly 271 is connected to the shaft 264 of the transfer drum 251, as shown in FIGS. 14A and 14B. A plurality of slots 276 are disposed in the driven gear 275 to engage a protrusion 274 of the drive gear 273. When the pen barrel 203 is turned relative to the storage assembly 211, a cannula 221 advances through the positions described above. Preferably, the gear assembly 271 is a Geneva gear mechanism.

A Geneva gear mechanism provides an intermittent option, i.e., index/dwell, for the transfer drum and cannula. Alternatives to a Geneva gear mechanism include cam arrangements that are typically used in parallel shaft indexers.

The rotary cam 281, as shown in FIGS. 11, 12 and 12A, is integral with the drive gear 273 of the gear assembly 271 and causes the advancement of the transfer slides 261. Retraction of the transfer slides 261 is caused by the rotary cam 281 in combination with a return spring 265 (FIG. 10).

Figure 22:
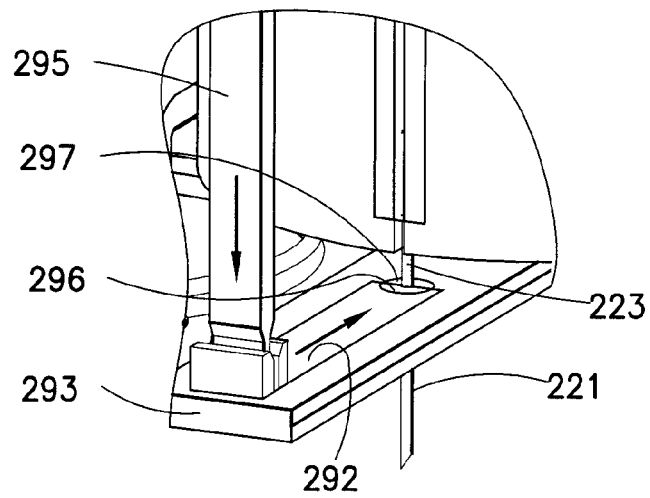
FIG. 22 is an enlarged perspective view of the hub jaw in an open position.
Figure 23:
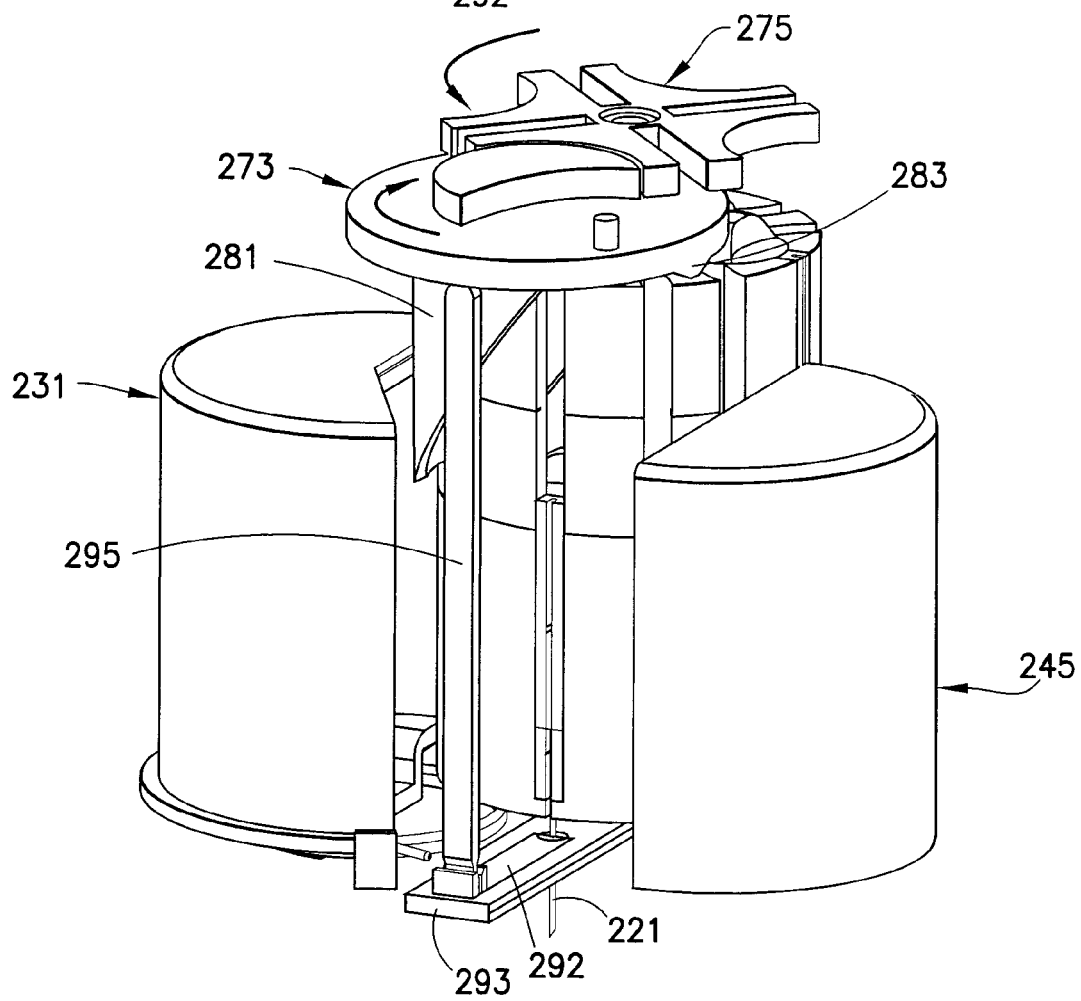
FIG. 23 is a perspective view of the storage assembly showing a fully advanced cannula.

A reusable cannula hub 291 includes two jaws 292 and 293 that are opened and closed to provide guidance, alignment, or a sealed fluid path, respectively, depending on the position of the cannula 221. The internal jaw 292 is disposed within the external jaw 293, as shown in FIG. 11. The fluid path extends from the drug vial 205 to the external hub jaw 293. Each of the hub jaws 292 and 293 has an elastomeric portion 296 and 297, as shown in FIGS. 22 and 23, respectively, that aligns with a cross-port 223 on the cannula 221 to provide a seal around the diameter of the cannula. Preferably, the elastomeric portions 296 and 297 are formed by overmolding.

The linear cam 295, or hub cam, as shown in FIGS. 11 and 12, controls the hub jaws 292 and 293 and is driven by a separate rotary cam 283 that is also integral with the drive gear 273 of the gear assembly 271. The hub jaws 292 and 293 are retained in a cavity located in the outer cover 213. The hub jaws 292 and 293 are spring loaded (not shown) to bias the hub jaws toward separation, i.e., the elastomeric portions 296 and 297 are spaced from each other. The linear cam 295 is used to close the hub jaws 292 and 293. The linear cam 295 engages the hub jaws 292 and 293 such that the opening between the hub jaws is centered on the injection axis 220, as shown in FIG. 17, in both the opened and closed positions. The linear cam 295 is upwardly spring loaded to remain in contact with the bottom surface of the drive gear 273. The secondary cam 283 extending from the drive gear 273 engages the linear cam 295 to advance the linear cam 295 and close the hub jaws 292 and 293 as the drive gear 273 rotates. As shown in FIGS. 12, 22 and 30, the end 290 of the linear cam 295 engages ramped surfaces 298 and 299 of the external and internal jaws 292 and 293, thereby moving the external and internal jaws to a closed position (i.e., the cannula 221 being sealed between the elastomeric portions 296 and 297 of the hub jaws 292 and 293).

Figure 15:
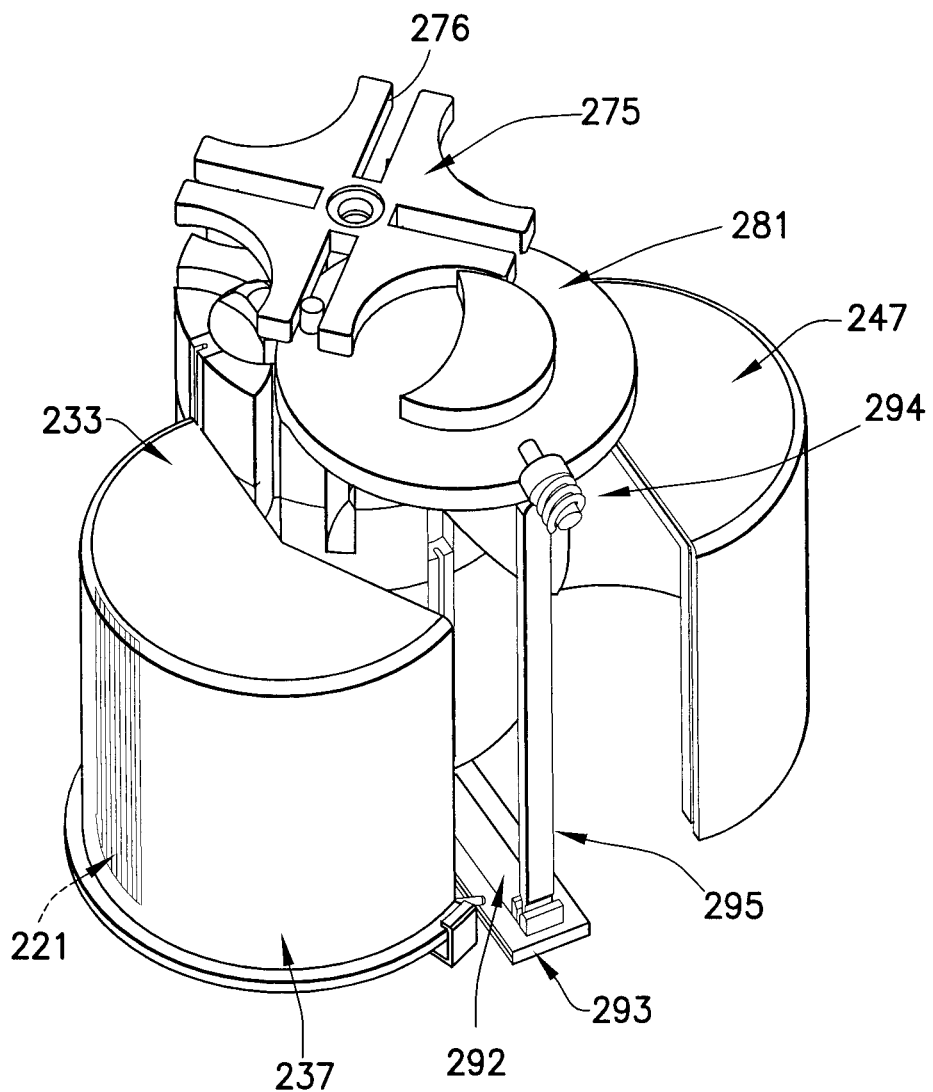
FIG. 15 is a perspective view from above of the assembled storage assembly of FIGS. 2A-2C without the outer cover.
Figure 18:
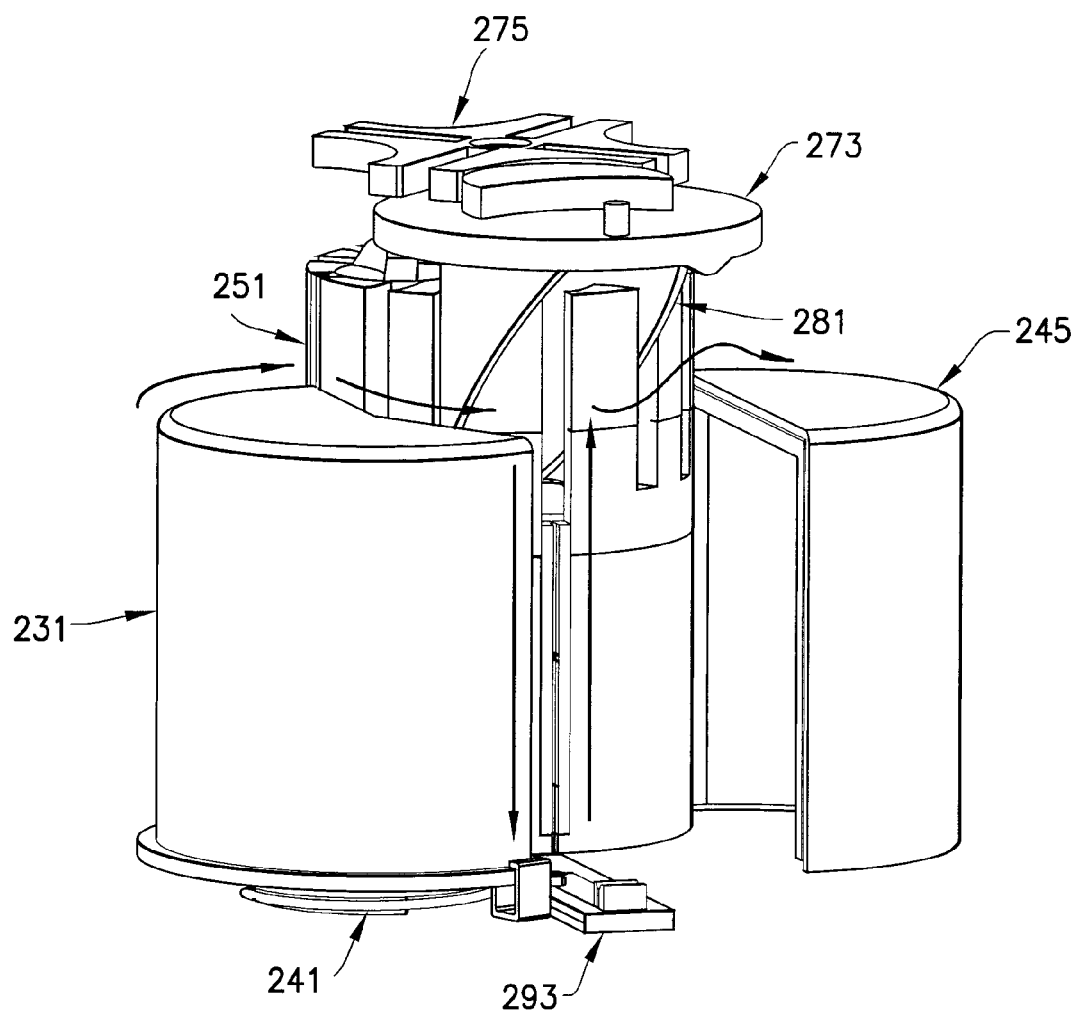
FIG. 18 is a perspective view of the storage assembly of FIG. 15 indicating operation of the storage assembly.
Figure 20:
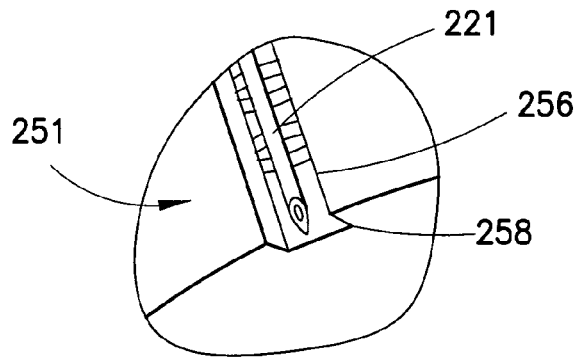
FIG. 20 is an enlarged perspective view showing spacing around a cannula disposed in the transfer drum.
Figure 21:
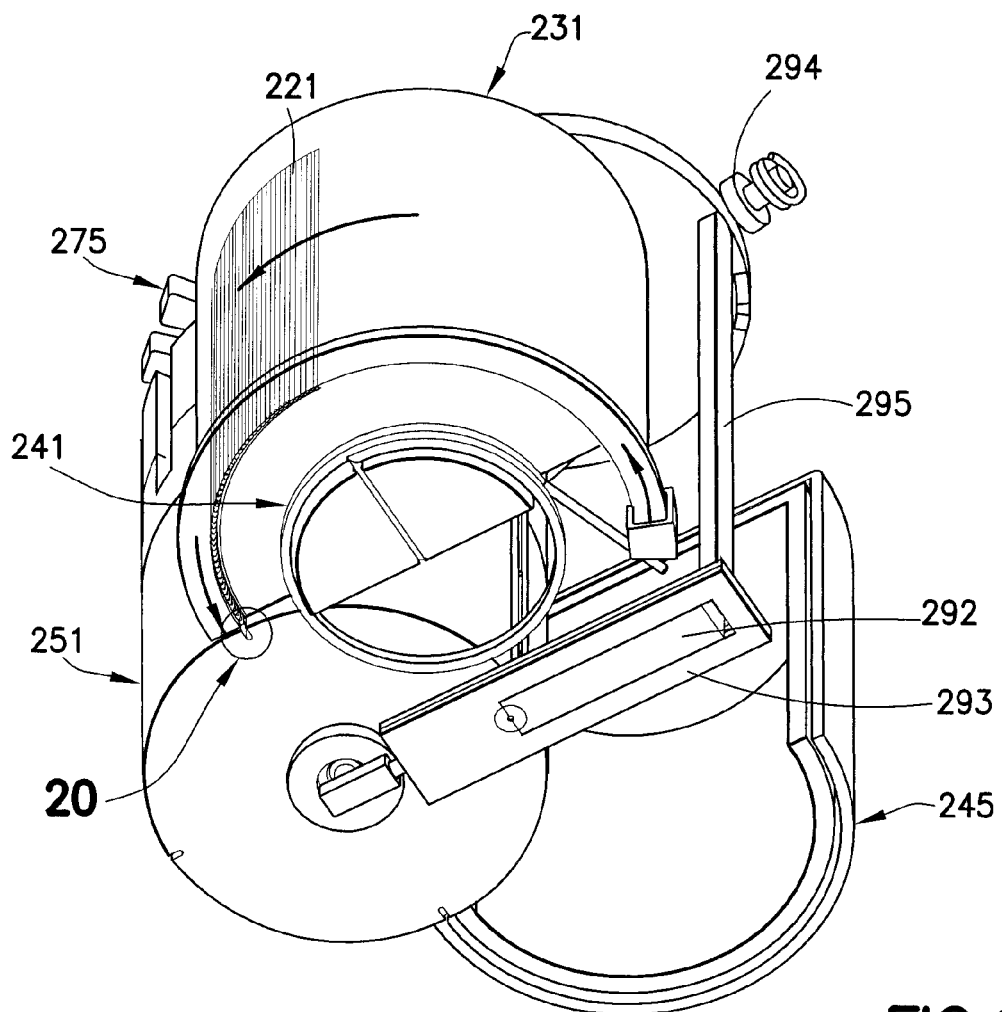
FIG. 21 is a perspective view from below of the revolver showing movement of the cannula from the in-feed subassembly to the transfer drum.

The storage assembly 211 operates in the following manner. The in-feed spring 241 provides back pressure on the line of cannulas 221 disposed in the in-feed assembly 231, as shown in FIG. 21. When the pen barrel 203 is turned relative to the storage assembly 211, the transfer drum 251 passes by the end of the in-feed assembly 231 and the lead-most cannula 221 advances into the middle slot 256 of a slide 261 in the transfer drum 251, as shown in FIGS. 15 and 18. The lower or sharp end 225 of the cannula 221 is generally aligned and guided by the slot 258 located at the bottom of the transfer drum 251, as shown in FIGS. 9 and 10. Alternatively, as shown in FIG. 20, the slot 258 in the base of the transfer drum 251 can be widened to provide guidance to an external feature on the cannula 221, e.g. an over-molded sleeve (as shown on the cannula 701 of FIG. 26F). The drive gear protrusion 274 engages the slot 276 in the driven gear 274, thereby rotating the transfer drum 251 and moving the cannula 221 in the transfer slide 261 from the pick-up position shown in FIG. 15 to the injection position shown in FIG. 17. The transfer drum 251 indexes approximately 90 degrees and dwells in a position aligned with the injection axis 220, as shown in FIG. 17. The transfer drum 251 dwells because after rotating approximately 90 degrees, the drive gear protrusion 274 exits the driven gear slot 276, thereby stopping rotation of the transfer drum 251 and putting the transfer drum in the dwell condition. The protrusion 274 engages the spring loaded pin 294, as shown in FIG. 16, thereby providing a positive stop for the drive gear 273 at the injection position.

As the rotation of the pen barrel 203 continues, the transfer slide 261 with the retained cannula 221 is contacted by the rotary cam 281 on the bottom of the drive gear 273 of the gear assembly 271, as shown in FIGS. 17 and 23. The transfer slide 261 advances such that the sharp end 225 of the cannula 221 passes through the two open jaws 292 and 293 of the reusable hub. After the transfer slide 261 is fully advanced, i.e., the cannula is advanced to the proper extension for an injection, the transfer slide dwells in the fully advanced position.

As the drive gear 273 is rotated to rotate the rotary cam 281, the second rotary cam 283 on the bottom of the drive gear 273 of the gear assembly 271 is also rotated. The second rotary cam 283 advances the linear cam (hub cam) 295 to close the jaws of the reusable hub around the cross-port 223 of the cannula 221, as shown in FIGS. 22 and 30. Further rotation of the drive gear is prevented by the protrusion 274 engaging the spring-loaded pin 294. An injection can now be made with the drug delivery pen 201.

Figure 28:
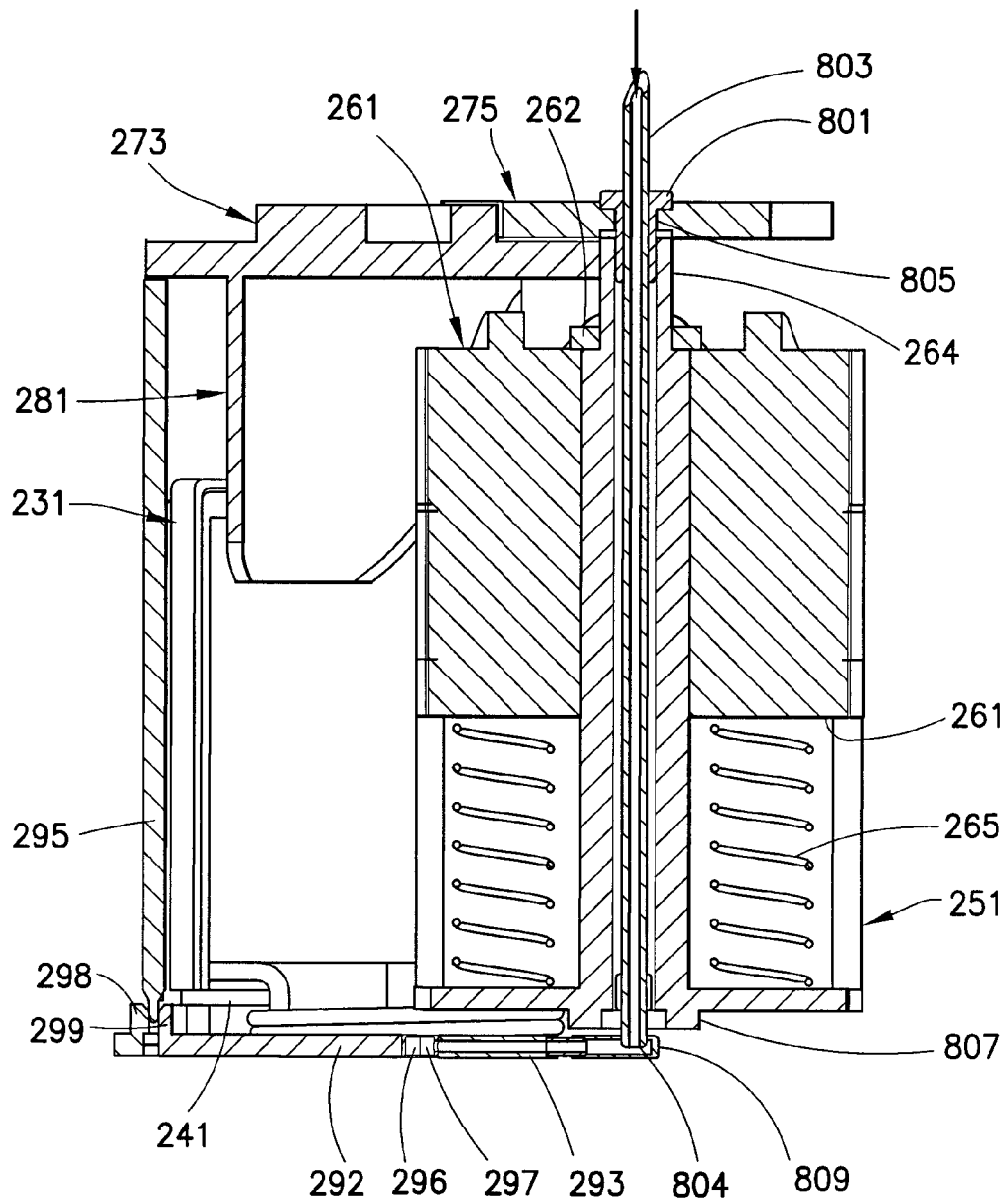
FIG. 28 is an elevational view in cross section of the storage assembly showing the fluid path in which the hub jaws in an open position.
Figure 29:
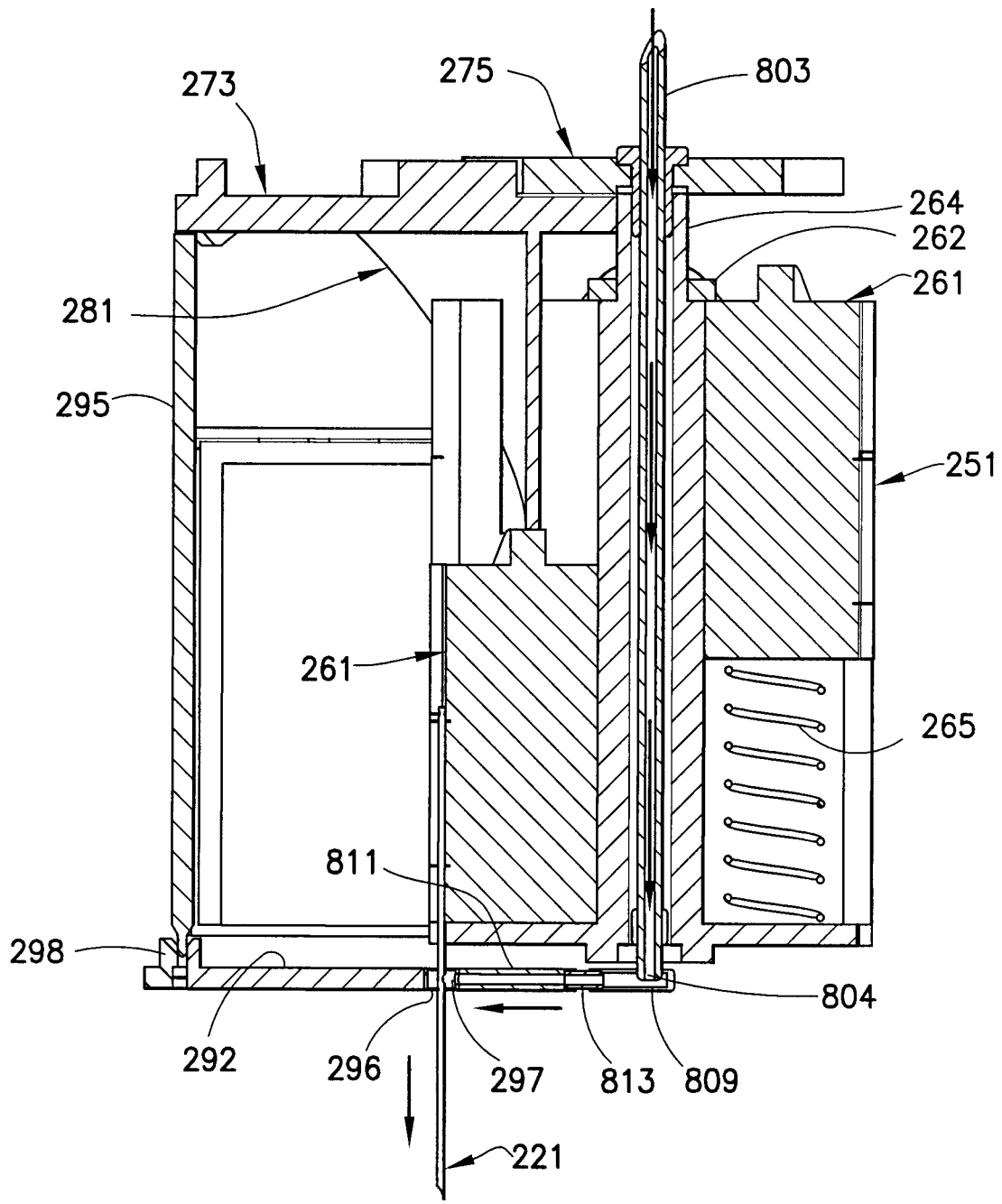
FIG. 29 is an elevational view in cross section of the storage assembly showing the fluid path in which the hub jaws are in a closed position.

The fluid path is shown in FIGS. 28-30. The drive gear 273 is rotated by rotation of the barrel 203 of the drug delivery pen 201 (FIGS. 2A-2C). Alternatively, a thumb-wheel can be connected to the drive gear to allow the user to actuate the storage assembly 211. A boss 801 engages the transfer drum shaft 264 and the housing outer cover 213 (FIG. 2C) to prevent rotation of a fluid needle 803, which passes through the shaft 264. A slip fit sleeve 805 locates the fluid needle 803 and facilitates alignment of the transfer drum 251. A transfer drum boss 807 engages the housing outer cover 213 (FIG. 2C) to further facilitate alignment of the transfer drum 251. One end of the fluid needle 803 is connected to a vial in the drug delivery pen in which the medicament to be delivered is stored. The other end 804 of the fluid needle 803 is connected to a fluid connector, as shown in FIGS. 28 and 29. The hub jaws 292 and 293 are in an open position in FIG. 28, i.e., the elastomeric portions 296 and 297 are spaced apart from one another.

When the hub jaws 292 and 293 are closed, as shown in FIGS. 29 and 30, the elastomeric portions 296 and 297 move together to seal the cannula 221 therebetween as described above. A telescoping sleeve 811 is molded in the external hub jaw 293 and connects the external hub jaw 293 to the fluid connector 809. The end 804 of the fluid needle 803 is preferably rounded to engage the fluid connector 809 through an O-ring, wipe seal or a septum. The telescoping sleeve 811 passes through a split septum 813 in the fluid connector 809.

As shown in FIGS. 29 and 30, a fluid path is created between the vial of the drug delivery pen 201 (FIG. 2C) and the cannula 221. The fluid passes from the vial, through the fluid needle 803 and into the fluid connector 809. When the hub jaws 292 and 293 are closed to create a seal with the cannula 221, the fluid passes from the fluid connector 809, through the sleeve 811, and into the cross-port 223 (FIG. 26A) in the cannula 221 such that medication can be delivered into the injection site.

Figure 25:
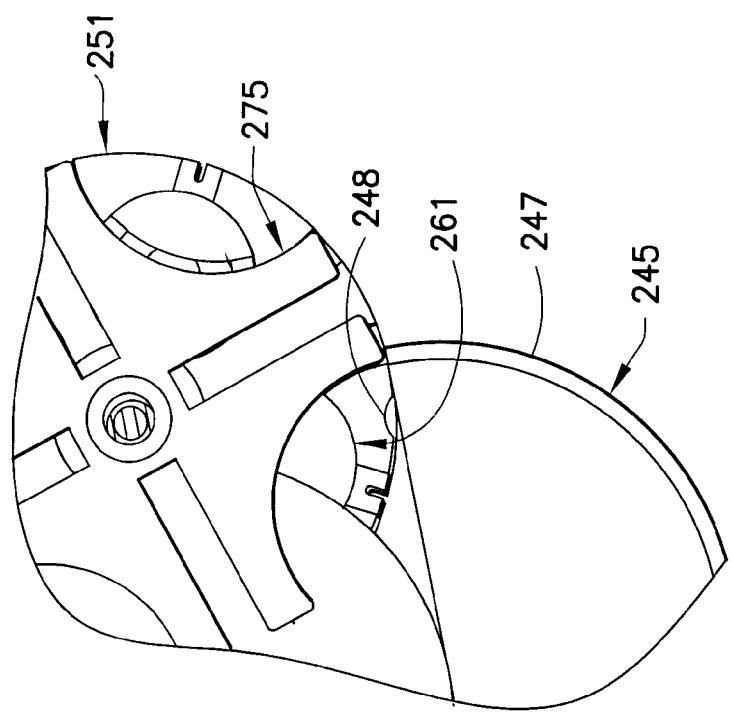
FIG. 25 is an enlarged top plan view of the storage assembly showing a used cannula being removed from the transfer drum.
Figure 24:
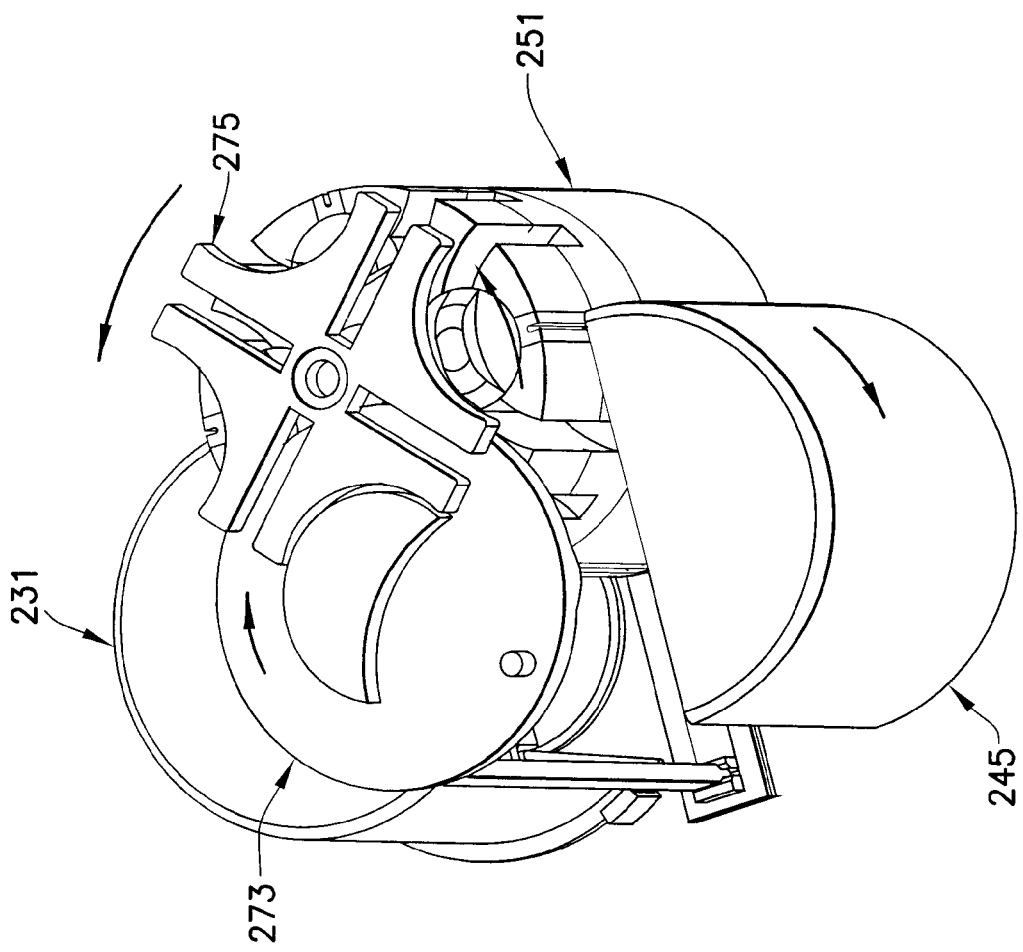
FIG. 24 is a perspective view from above of the storage assembly showing movement of the transfer drum and cannula.
Figure 27:
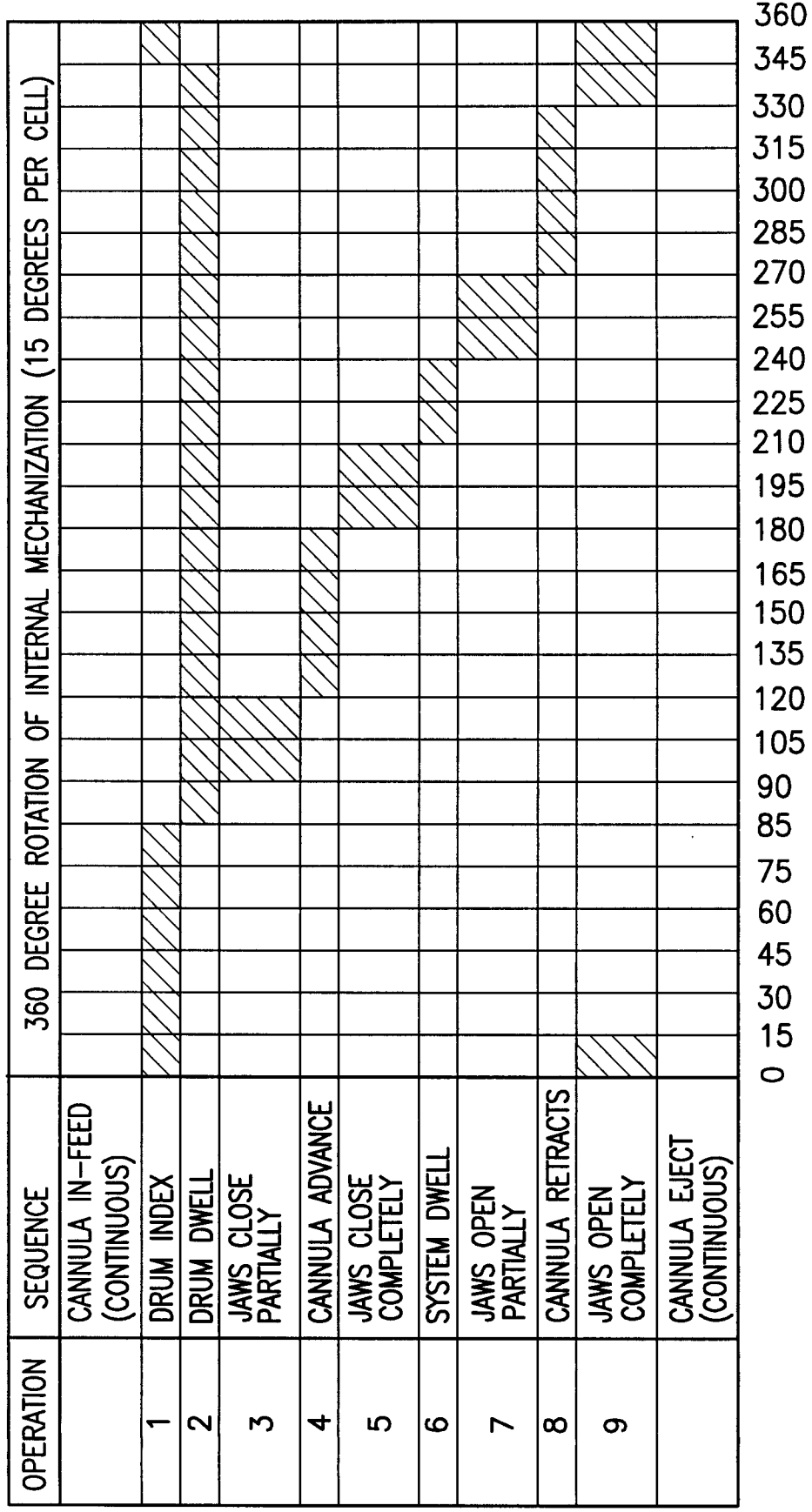
FIG. 27 is a table indicating movement of the components of the storage assembly during operation.

After an injection has been made, the user releases a manual latch, such as the spring pin 294, to enable further rotation of the pen barrel 203 from the stopped position shown in FIG. 16. As the pen barrel 203 is further rotated, the jaws of the reusable hub are opened, the used cannula 221 is retracted by the return spring 265, which pushes the transfer slide 261 upwardly, the transfer drum 251 indexes, and the used cannula 221 is removed from the transfer drum 251 and is transferred to the out-feed assembly 245, as shown in FIGS. 24 and 25. At least one finger 248 disposed on the out-feed cover 247, as shown in FIGS. 4-6 and 25, pulls the used cannula 221 from the transfer slide 261 into the track formed between the out-feed cover 247 and the out-feed guide 249. Used cannulas 221 are stored in the out-feed assembly until the storage assembly 221 is discarded. One 360-degree rotation of the pen barrel 203 relative to the storage assembly 211 provides a complete index/advance/retract/eject cycle, as detailed in FIG. 27.

To properly advance the cannula 221 on the in-feed and out-feed tracks, each cannula contacts the adjacent cannula at a minimum of two points on the outer surface of the cylindrical envelope that are at a distance of approximately 60% to 70% of the cannula length apart. Cannula features, such as for guidance, alignment and fluid path, are preferably within this cylindrical envelope. For a hubless cannula (FIGS. 26A, 26B and 26D), such additional features for guidance, alignment and fluid path are preferably internal to the 0.010 inch or 0.025 cm diameter cylindrical envelope.

An alternative configuration of the out-feed track is an out-feed chamber (not shown) or a short escapement leading to a chamber. As the transfer drum 251 rotates to the out-feed track, the fingers in the track shed the used cannula from the transfer drum, and as the cannula 221 advances it enters the chamber.

The storage assembly can include features to prevent each cannula from being used more than once. A fluid gate or two-way valve (not shown) located in the fluid path or the external hub jaw is closed during or at the end of each injection cycle. The manually actuated latch that enables further rotation of the device following an injection (or for ensuing rotary motion) is used to reset the gate controlling the fluid flow. Alternately, the storage assembly can be used with a "smart" insulin pen, which includes electrical circuitry to prevent reuse of a used cannula.

Figure 1A:
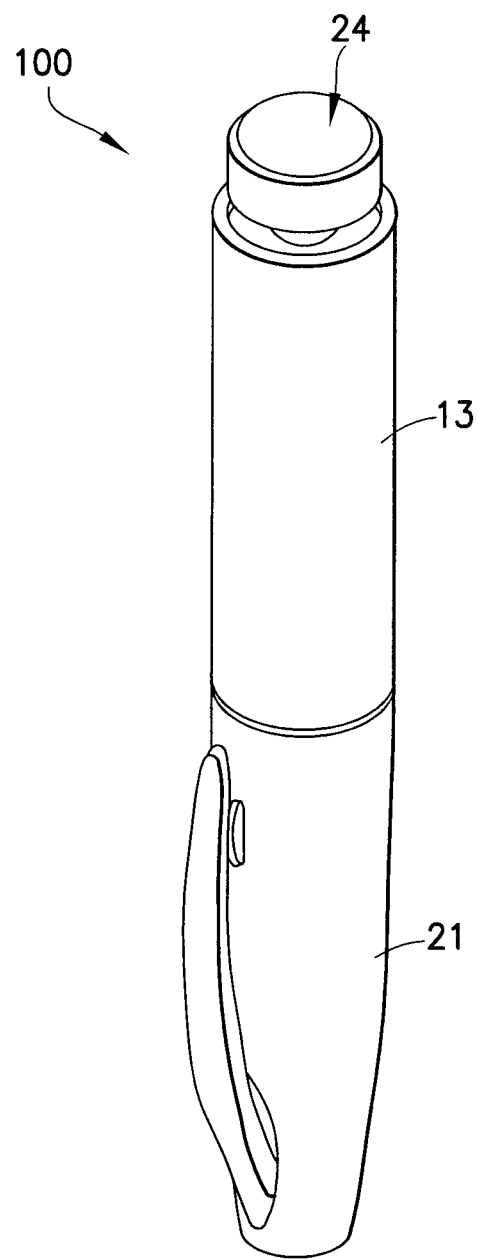
FIGS. 1A and 1B are perspective and exploded perspective views, respectively, of a drug delivery pen.
Figure 1B:
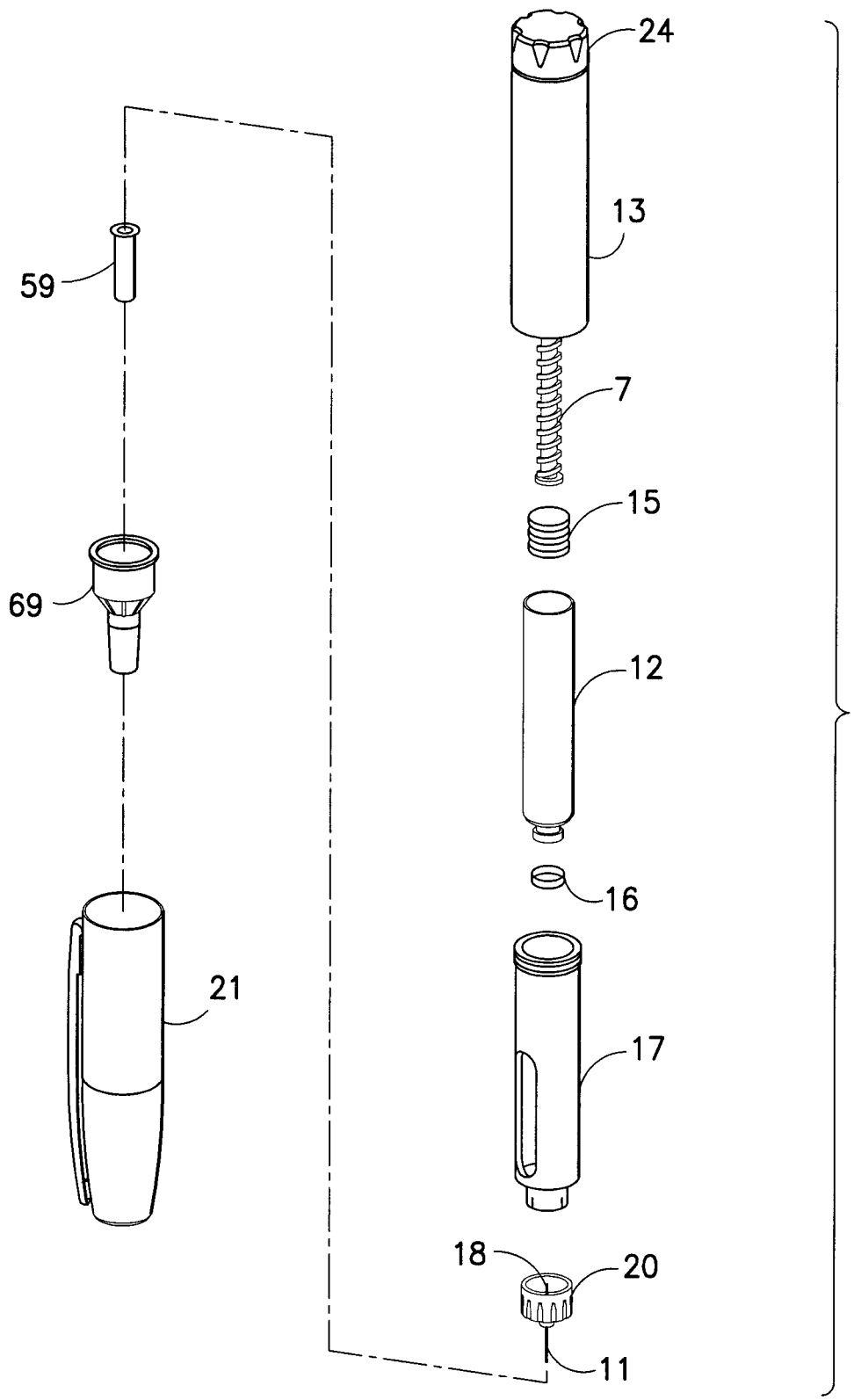

The storage assembly in accordance with exemplary embodiments of the present invention does not require that the cannulas be over-molded or attached to a larger diameter hub as with existing pen needles 20 (FIG. 1B). The storage assembly transfers small-gauge cylinders and tubes. FIGS. 26A-26F show various cannula configurations for use with the storage assembly. Slight modification of the storage assembly may be required depending on the configuration of the cannula. The cannulas can be modified with additional features, which are preferably within the cylindrical envelope of the cannula, to facilitate proper control and transfer thereof. For example, as shown in FIGS. 26A and 26D, the cannula can have a cross or side port through which fluid flows to provide a fluid path adjacent to the sharp end of the cannula. As shown in FIGS. 26A, 26D, 26E and 26F, the cannula can have grooves to maintain the alignment and position of the cannula in the storage assembly and to retain the cannula during retraction.

The cannula 221 can have a groove 225 located a short distance from the square end 226, as shown in FIG. 26A. The groove 225 stops fluid flow from the square end 226 of the cannula 221, and also provides annular engagement with the transfer mechanism of the storage assembly 211. A cross-port 223 in the cannula 201 provides a fluid path for fluid flow through the cannula 221.

As shown in FIG. 26B, a cannula is provided with a first sharp end 303 for making an injection. Plastic over-molded hubs 307 and 309 are disposed on the cannula 301 to allow more liberal tolerances for the components of the storage assembly.

Another exemplary embodiment of a cannula 401, as shown in FIG. 26C, includes a pierced end 403 and a metal sleeve 407 laser-tacked to the cannula 401 to allow more liberal tolerances for the components of the storage assembly.

Additional grooves can be formed in the cannula to increase engagement, such as shown in the cannula 501 of FIG. 26D. The cannula 501 has a first groove 503 proximal the square end 504 of the cannula. A second groove 505 is formed above the cross-port 507. The second groove 505 above the cross-port 507 substantially eliminates excess fluid flow into the sealed, upper portion of the cannula and substantially prevents drooling from compression of the void volume in the sealed portion of the cannula 501.

Another exemplary embodiment of a cannula 601, as shown in FIG. 26E, includes a plurality of over-molded plastic hubs 603 and 605. A groove 609 is disposed between the two ends of hub 605 to provide engagement with the transfer mechanism.

Another exemplary embodiment of a cannula 701, as shown in FIG. 26F, includes an overmolded plastic hub 703 that extends along a majority of the axial length of the cannula. A groove 709 is disposed in the plastic hub 703 distal the sharp end 707 for engaging with the transfer mechanism.

An injection device can include a powered user interface to exchange a cannula disposed in the injection device. The powered user interface can include a battery for supplying power, a push button to manually control the cannula exchange, and a control circuit between the push button and the battery to operate the exchange when the button is pushed.

As an alternative to the two elastomer-coated hub jaws, a single elastomer annular ring can be disposed on the cannula. The cam actuated jaws compress the annular ring against the outer surface of the cannula, thereby providing a sealed fluid path.

In another exemplary embodiment, the cannula pierces through two septa. When the cannula is fully advanced the cross-port in the cannula is disposed between the two septa, thereby allowing fluid flow.

As an alternative to the gear assembly, a parallel shaft indexer can be used to provide the same index/dwell motion as the gear assembly.

The cannulas can be retained in the transfer slides by spring-loaded elements such that a user can extract a bent cannula from the storage assembly.

Linear and rotary cams can be used for positive (advancing) motions and spring return for negative (retracting) motions. The rise and fall, contact angles between cam surfaces, and cam timing can be based on commonly accepted design standards for machine cams operating at low to moderate speeds, e.g., 100 to 300 rpm.

The priming volume is minimized because the fluid path internal to the cannula extends only from the sharp end of the cannula to the cross-port. Drooling can be minimized by reducing the void volume and the fluid volume in the cannula. Drooling can be further minimized by incorporating a check valve in the fluid path adjacent to the cannula cross-port, for example, in the external hub jaw.

The cannula 221, as shown in FIG. 26A, can have a diameter of approximately 0.010 inches (0.025 cm) and a length of approximately 0.70 inches (1.78 cm). An overall length of the storage assembly 211 (FIGS. 2A-2C) can be approximately 1.50 inches (3.81 cm) wide, 1.00 inch (2.54 cm) deep and 1.75 inches (4.45 cm) high. These dimensions for the storage assembly can be reduced by hollowing the in-feed and out-feed assemblies to allow them to fit closely to the outer diameter of the transfer drum.

In an exemplary embodiment of the present invention, each new (i.e., prior to being used for an injection) cannula, stored in the in-feed assembly is individually sterile, thereby preventing contamination of a new cannula by a used cannula. For example, a sterility barrier is provided for each new cannula. For example, at the end of the manufacturing and assembly process, the top cover 215 is sealed to the outer cover 213, thereby sterilizing the storage assembly 211, i.e., each of the cannulas is individually sterile. The sterile cannula are stored in the in-feed assembly 231 and the used cannula are transferred to and stored in the out-feed assembly 245. To ensure cross-contamination does not occur, the transfer slides 261 contact the portion of the cannula that does not penetrate tissue during an injection. The hub jaws 292 and 293 also contact the portion of the cannula that does not penetrate tissue during an injection, i.e., the hub jaws open prior to retraction of the cannula 221.

In another exemplary embodiment of the present invention, each used cannula remains accessible such that the user has access to the used cannulas in case of an emergency. Alternatively, only the last cannula is always accessible, thereby providing an available cannula in case of emergency.

While the foregoing detailed description refers to the drawings that show a storage assembly 211 in accordance with exemplary embodiments of the present invention for use with a drug delivery pen 201, as shown in FIGS. 2A-2C, the present invention is equally applicable to a storage assembly for storing stylets for use with a lancer. The stylet storage assembly can be either integrally formed with or removably connected to the lancer. The stylet storage assembly is substantially similar to the foregoing description of the cannula storage assembly.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

What is claimed is:

1. A storage assembly, comprising:
   a housing connectable to a drug delivery device;
   a first chamber disposed in said housing;
   a plurality of penetrating members stored in said first chamber;
   a second chamber disposed in said housing for storing said plurality of penetrating members after being used in an injection;
   a transfer drum disposed in said housing for transferring one of said penetrating members from said first chamber to an injection position and from said injection position to said second chamber following an injection; and
   a spring biasing said plurality of penetrating members to a position to be transferred from said first chamber to said transfer drum.

2. The storage assembly according to claim 1, comprising:
   a drug delivery device connected to said housing as part of said combination.

3. The storage assembly according to claim 1, wherein
   a drive gear having a protrusion is connected to the drug delivery device and a driven gear having a plurality of slots is connected to said transfer drum, such that rotation of said drive gear rotates said driven gear when said protrusion engages one of said plurality of slots.

4. The storage assembly according to claim 3, wherein
   a fluid connector disposed in said housing is in fluid communication with the drug delivery device, said fluid connector being in fluid communication with said penetrating member when said penetrating member is in said second position.

5. The storage assembly according to claim 4, wherein
   a seal is formed around a connection between said fluid connector and said penetrating member when said penetrating member is in said second position.

6. The storage assembly according to claim 5, wherein
   a linear cam is engaged by a hub cam on said drive gear to create said seal around said penetrating member.

7. The storage assembly according to claim 6, wherein
   a port in a side of said penetrating member is in fluid communication with said fluid connector when said penetrating member is in said second position.

8. The storage assembly according to claim 3, wherein
   a stop member is engaged by said drive gear protrusion to stop further rotation of said drive gear when said penetrating member is in said second position.

9. The storage assembly according to claim 8, wherein
   said stop member is manually released to allow further rotation of said drive gear.

10. The storage assembly according to claim 1, wherein
    said transfer drum comprises a plurality of openings; and
    a transfer slide is movably disposed in each of said plurality of openings and is adapted to receive one of said penetrating members from said first chamber, said transfer slide being movable between a first position in which said penetrating member is within said housing and a second position in which said penetrating member extends from said housing drum to perform the injection.

11. The storage assembly according to claim 10, wherein
    a spring biases said transfer slide to said first position.

12. The storage assembly according to claim 11, wherein
    a retaining ring connected to said transfer drum limits movement of said transfer slide back to said first position by said spring.

13. The storage assembly according to claim 10, wherein
    a rotary cam connected to said drive gear moves said transfer slide from said first position to said second position.

14. A storage assembly, comprising:
    a housing connectable to a drug delivery device;
    a first chamber disposed in said housing;
    a plurality of penetrating members stored in said first chamber;
    a second chamber disposed in said housing for storing said plurality of penetrating members after being used in an injection; and
    a transfer drum disposed in said housing for transferring one of said penetrating members from said first chamber to an injection position and from said injection position to said second chamber following an injection;
    wherein
    said transfer drum comprises a plurality of openings;
    a transfer slide is movably disposed in each of said plurality of openings and is adapted to receive one of said penetrating members from said first chamber, said transfer slide being movable between a first position in which said penetrating member is within said housing and a second position in which said penetrating member extends from said housing drum to perform the injection; and
    a finger extends outwardly from said second chamber to facilitate transfer of said penetrating member from said transfer slide of said transfer drum to said second chamber.

15. A method of performing an injection with a drug delivery device, comprising the steps of:
    biasing said plurality of penetrating members to a position to be transferred from said first chamber to said transfer drum;
    transferring one of a plurality of penetrating members from a first chamber to a transfer drum by rotating the drug delivery device;
    moving the transferred penetrating member to an injection position by continued rotation of the drug delivery device;
    injecting a medicament from the drug delivery device through the transferred penetrating member into an injection site; and
    transferring the used penetrating member to a second chamber.

16. The method of performing an injection with a drug delivery device according to claim 15, further comprising
    preventing further rotation of the drug delivery device when the penetrating member is in the injection position.

17. The method of performing an injection with a drug delivery device according to claim 16, wherein
    preventing further rotation of the drug delivery device comprises engaging a drive gear connected to the drug delivery pen with a latch.

18. The method of performing an injection with a drug delivery device according to claim 17, further comprising releasing the latch to perform another injection.

19. The method of performing an injection with a drug delivery device according to claim 15, further comprising
discarding the second chamber of used penetrating members when all of the penetrating members stored in the first chamber have been used.

20. A storage assembly, comprising:
a housing connectable to a drug delivery device;
a first chamber disposed in said housing;
a plurality of penetrating members stored in said first chamber;
a second chamber disposed in said housing for storing said plurality of penetrating members after being used in an injection; and
a transfer drum disposed in said housing for transferring one of said penetrating members from said first chamber to an injection position and from said injection position to said second chamber following an injection,
wherein:
said transfer drum comprises a plurality of openings;
a transfer slide is movably disposed in each of said plurality of openings and is adapted to receive one of said penetrating members from said first chamber, said transfer slide being movable between a first position in which said penetrating member is within said housing and a second position in which said penetrating member extends from said housing drum to perform the injection;
a spring biases said transfer slide to said first position; and
a retaining ring connected to said transfer drum limits movement of said transfer slide back to said first position by said spring.

21. A storage assembly, comprising:
a housing connectable to a drug delivery device;
a first chamber disposed in said housing;
a plurality of penetrating members stored in said first chamber;
a second chamber disposed in said housing for storing said plurality of penetrating members after being used in an injection; and
a transfer drum disposed in said housing for transferring one of said penetrating members from said first chamber to an injection position and from said injection position to said second chamber following an injection,
wherein:
a drive gear having a protrusion is connected to the drug delivery device and a driven gear having a plurality of slots is connected to said transfer drum, such that rotation of said drive gear rotates said driven gear when said protrusion engages one of said plurality of slots;
a fluid connector disposed in said housing is in fluid communication with the drug delivery device, said fluid connector being in fluid communication with said penetrating member when said penetrating member is in said second position;
a seal is formed around a connection between said fluid connector and said penetrating member when said penetrating member is in said second position; and
a linear cam is engaged by a hub cam on said drive gear to create said seal around said penetrating member.

22. The storage assembly according to claim 21, wherein a port in a side of said penetrating member is in fluid communication with said fluid connector when said penetrating member is in said second position.

* * * * *